(12) United States Patent
Clarke et al.

(10) Patent No.: US 11,213,401 B2
(45) Date of Patent: *Jan. 4, 2022

(54) IMPLANT FOR A BONE JOINT

(71) Applicant: National University of Ireland, Galway, Galway (IE)

(72) Inventors: Gerry Clarke, County Galway (IE); Brendan Boland, County Kildare (IE); Mark Bruzzi, Galway (IE); Amy L. Ladd, Stanford, CA (US); Arnold-Peter C. Weiss, Barrington, RI (US); Filip Stockmans, Heule Kortrijk (BE)

(73) Assignee: National University of Ireland, Galway, Galway (IE)

( * ) Notice: Subject to any disclaimer, the term of this patent is extended or adjusted under 35 U.S.C. 154(b) by 67 days.

This patent is subject to a terminal disclaimer.

(21) Appl. No.: 16/271,452

(22) Filed: Feb. 8, 2019

(65) Prior Publication Data

US 2019/0167437 A1 Jun. 6, 2019

Related U.S. Application Data

(63) Continuation of application No. 15/429,635, filed on Feb. 10, 2017, now Pat. No. 10,265,186.

(30) Foreign Application Priority Data

Feb. 10, 2016 (EP) ..................... 16155090

(51) Int. Cl.
*A61F 2/42* (2006.01)
*A61F 2/30* (2006.01)

(52) U.S. Cl.
CPC .............. *A61F 2/4241* (2013.01); *A61F 2/30* (2013.01); *A61F 2002/3055* (2013.01);
(Continued)

(58) Field of Classification Search
CPC ...... A61F 2/32; A61F 2/40; A61F 2/42; A61F 2/4225; A61F 2/4241; A61F 2002/30649;
(Continued)

(56) References Cited

U.S. PATENT DOCUMENTS

| 3,916,451 A | 11/1975 | Buechel et al. |
| 4,213,208 A | 7/1980 | Marne |

(Continued)

FOREIGN PATENT DOCUMENTS

| CN | 103815989 A | 5/2014 |
| EP | 0322493 A1 | 7/1989 |

(Continued)

OTHER PUBLICATIONS

European Search Report for European Application No. 19167519.8, dated Sep. 12, 2019 (7 pages).

(Continued)

*Primary Examiner* — Brian A Dukert
(74) *Attorney, Agent, or Firm* — Bookoff McAndrews, PLLC

(57) ABSTRACT

An implant (30) for a mammalian bone joint (3) for spacing a first bone (2) of the joint from a second bone (1) of the joint while allowing translational movement of the second bone in relation to the first bone is described. The implant comprises (a) a distal part (31) configured for intramedullary engagement with an end of the second bone, (b) a proximal part (34) having a platform (15) configured for non-engaging abutment of an end of the first bone and translational movement thereon, and (c) an articulating coupling (10, 16) provided between the distal and proximal ends allowing controlled articulation of the first and second bones. The bone-abutting platform is shaped to conform to and translate upon the end of the first bone. A kit for assembly to form the (Continued)

implant of the invention, and the use of the implant to treat osteoarthritis in a bone joint, are also described.

14 Claims, 18 Drawing Sheets

(52) U.S. Cl.
CPC .............. *A61F 2002/30065* (2013.01); *A61F 2002/30301* (2013.01); *A61F 2002/30331* (2013.01); *A61F 2002/30378* (2013.01); *A61F 2002/30604* (2013.01); *A61F 2002/30649* (2013.01); *A61F 2002/4253* (2013.01); *A61F 2002/4258* (2013.01); *A61F 2310/00017* (2013.01); *A61F 2310/00023* (2013.01); *A61F 2310/00029* (2013.01); *A61F 2310/00059* (2013.01); *A61F 2310/00089* (2013.01); *A61F 2310/00161* (2013.01); *A61F 2310/00173* (2013.01)

(58) Field of Classification Search
CPC ...... A61F 2002/4243; A61F 2002/4251; A61F 2002/4253; A61F 2002/4256; A61F 2002/4258
See application file for complete search history.

(56) References Cited

U.S. PATENT DOCUMENTS

| | | | |
|---|---|---|---|
| 4,685,919 A | | 8/1987 | Niwa et al. |
| 5,147,386 A | | 9/1992 | Carignan et al. |
| 5,458,601 A | | 10/1995 | Young et al. |
| 5,593,445 A | | 1/1997 | Waits |
| 6,206,925 B1 | | 3/2001 | Tornier |
| 6,284,000 B1 | * | 9/2001 | Ege ........................ A61F 2/4261 623/21.11 |
| 7,011,686 B2 | | 3/2006 | Ball et al. |
| 7,033,396 B2 | * | 4/2006 | Tornier ..................... A61F 2/32 623/19.11 |
| 8,303,664 B1 | | 11/2012 | Burstein et al. |
| 2005/0033426 A1 | | 2/2005 | Ogilvie et al. |
| 2006/0041314 A1 | | 2/2006 | Millard |
| 2006/0074492 A1 | | 4/2006 | Frey |
| 2008/0221698 A1 | | 9/2008 | Berger |
| 2009/0112328 A1 | | 4/2009 | Tornier et al. |
| 2010/0010637 A1 | * | 1/2010 | Pequignot ............. A61F 2/4241 623/21.15 |
| 2013/0150975 A1 | | 6/2013 | Iannotti et al. |
| 2013/0197655 A1 | | 8/2013 | Scheker |
| 2013/0338784 A1 | | 12/2013 | Pallia |
| 2014/0074246 A1 | | 3/2014 | Huebner |
| 2018/0214276 A1 | | 8/2018 | Humphrey |

FOREIGN PATENT DOCUMENTS

| | | |
|---|---|---|
| EP | 2749256 A1 | 7/2014 |
| EP | 3205311 A1 | 8/2017 |
| FR | 2 805 152 A1 | 8/2001 |
| FR | 2805151 A1 | 8/2001 |
| FR | 2900045 A1 | 10/2007 |
| FR | 2912051 | 8/2008 |
| FR | 2 931 059 A1 | 11/2009 |
| FR | 3 027 213 A1 | 4/2016 |
| WO | WO 2014/077750 A1 | 5/2014 |
| WO | WO 2015/088403 A1 | 6/2015 |
| WO | WO 2017/137607 A2 | 8/2017 |

OTHER PUBLICATIONS

International Search Report and Written Opinion for International Application No. 2019/0058, completed Jun. 25, 2019 (8 pages).
"TIE-IN™ Trapezium Implant—A Comprehensive Solution for CMC," Wright Medical Group N.V., Jul. 30, 2016.
Summary of Safety and Effectiveness, TIE-IN™ Trapezium, Wright Medical Group, Nov. 7, 2003.
International Search Report and Written Opinion for International Application No. PCT/EP2020/055344, dated May 13, 2020 (12 pages).
International Search Report and Written Opinion for International Application No. PCT/EP2020/055353, dated May 13, 2020 (6 pages).
International Search Report and Written Opinion for International Application No. PCT/EP2017/053079, dated Aug. 23, 2017 (11 pages).
J. Crisco et al., "In Vivo Kinematics of the Trapeziometacarpal Joint During Thumb Extension-Flexion and Abduction-Adduction," J Hand Surg Am., 2015, vol. 40 (2), pp. 289-296.
De Aragon, J.S.M et al., "Early Outcomes of Pyrolytic Carbon Hemiarthroplasty for the Treatment of Trapezial-Metacarpal Arthritis," J Hand Surg Am., 2009, vol. 34A (2), pp. 205-212.
Krukhaug, Y. et al., "The results of 479 thumb carpometacarpal joint replacements reported in the Norwegian Arthroplasty Register," J Hand Surg Am., 2014, vol. 39 (8), pp. 1-7, http://jhs.sagepub.com/content/early/2014/04/29/1753193413513988.
Naidu, S.H. et al., "Titanium Based Joint Arthroplasty: A Finite Element Analysis and Clinical Study," J Hand Surg Am., 2006, vol. 31 (5), pp. 760-765.
Pritchett, J.W. et al., "A Promising Thumb Basal Joint Hemiarthroplasty for Treatment of Trapeziometacarpal Osteoarthritis," Clinical Orthopaedics and Related Research, 2012, 470 (10), pp. 2756-2763.
Turker, T. et al., "Trapezio-metacarpal arthritis: The price of an opposable thumb!," Indian Journal of Plastic Surgery, 2011, vol. 44, Issue 2, 9 pgs.

* cited by examiner

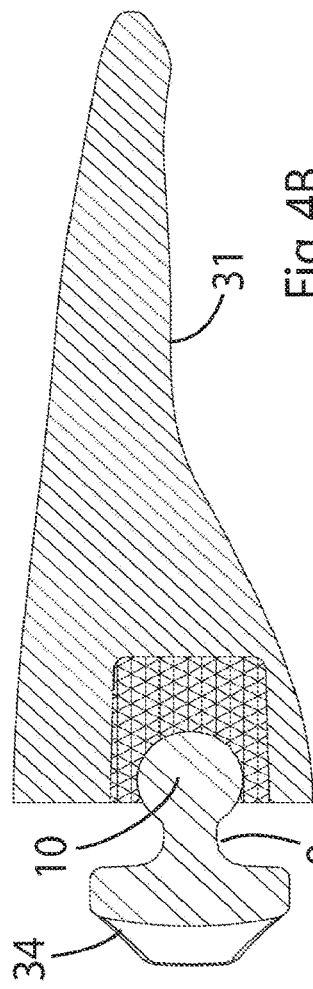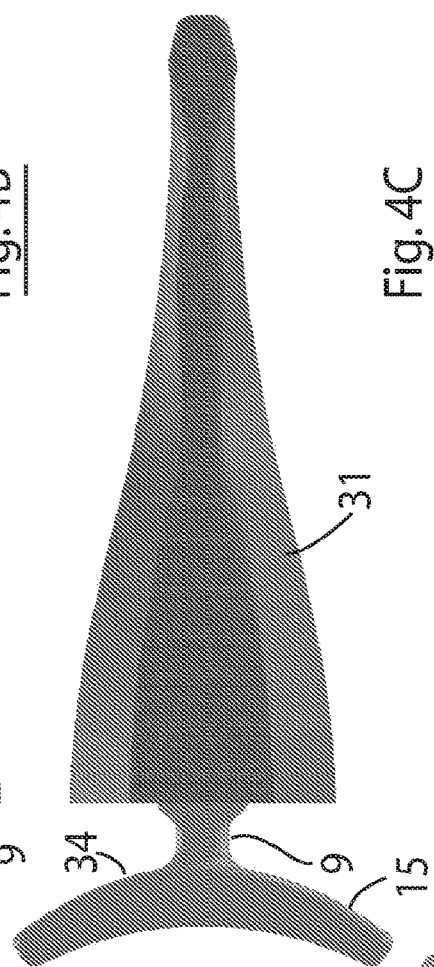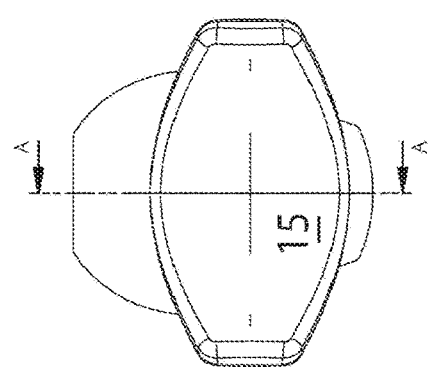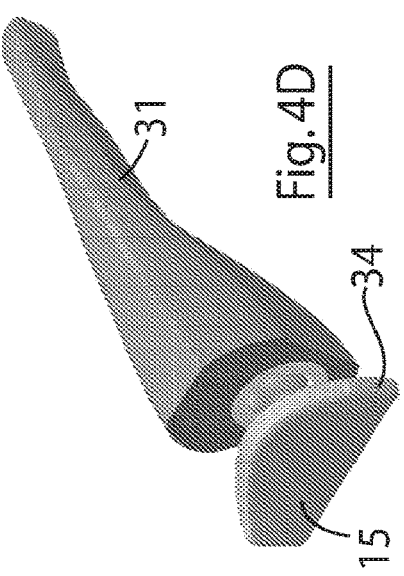

Metacarpal base resection. No trapezium resection

Broach used to form placement position of metacarpal stem

Metacarpal stem insertion by interference fit

Trapezial base is saddle-shaped and abuts the trapezium
Trapezial base slides over i.e. articulates with the trapezium
Ball and socket articulation in the metacarpal
Both articulations are separated in space and can function independently and concurrently Trapezial base abuts and slides over trapezium
Metacarpal movement causes articulation at the ball and socket
Metacarpal movement causes articulation at the trapezial base/trapezium interface

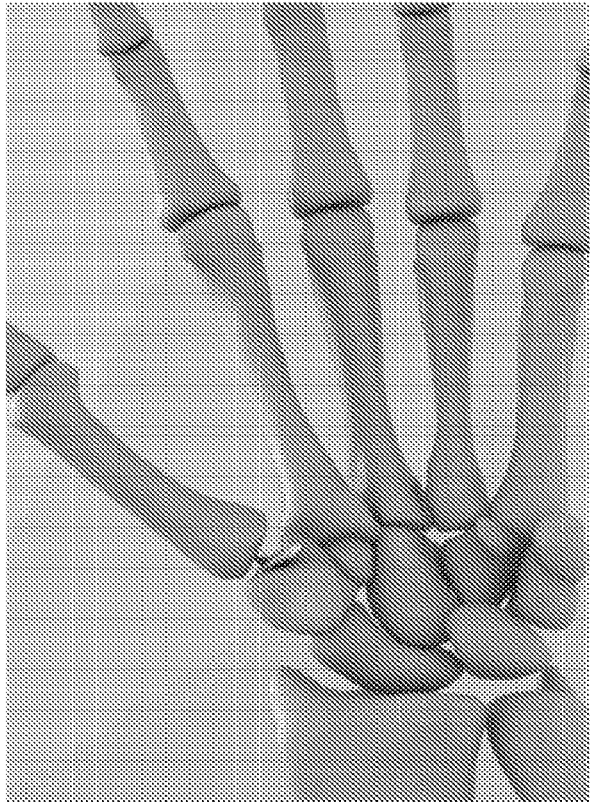

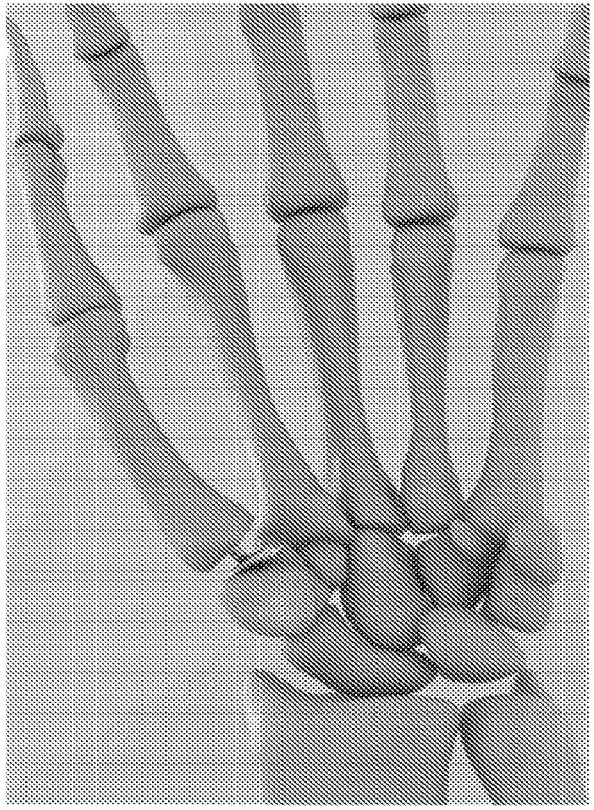

Images show alteration in trapezial base as per movement of the metacarpal
Movement of the device occurs preferentially at the ball and socket during abduction-adduction of the metacarpal
Movement of the device occurs preferentially at the trapezial base during extension-flexion
The device does not have to reconfigure in size or shape to accommodate different movements

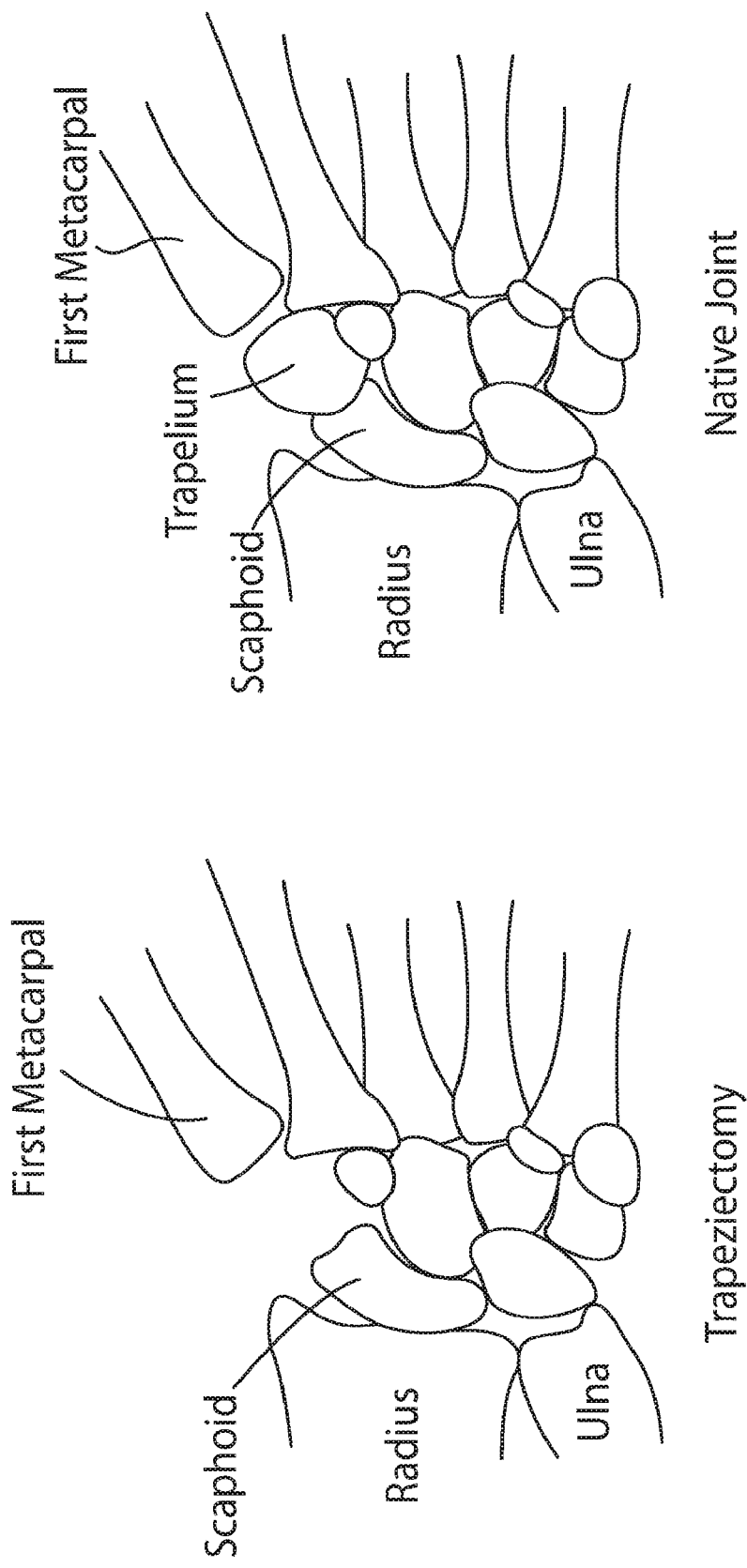

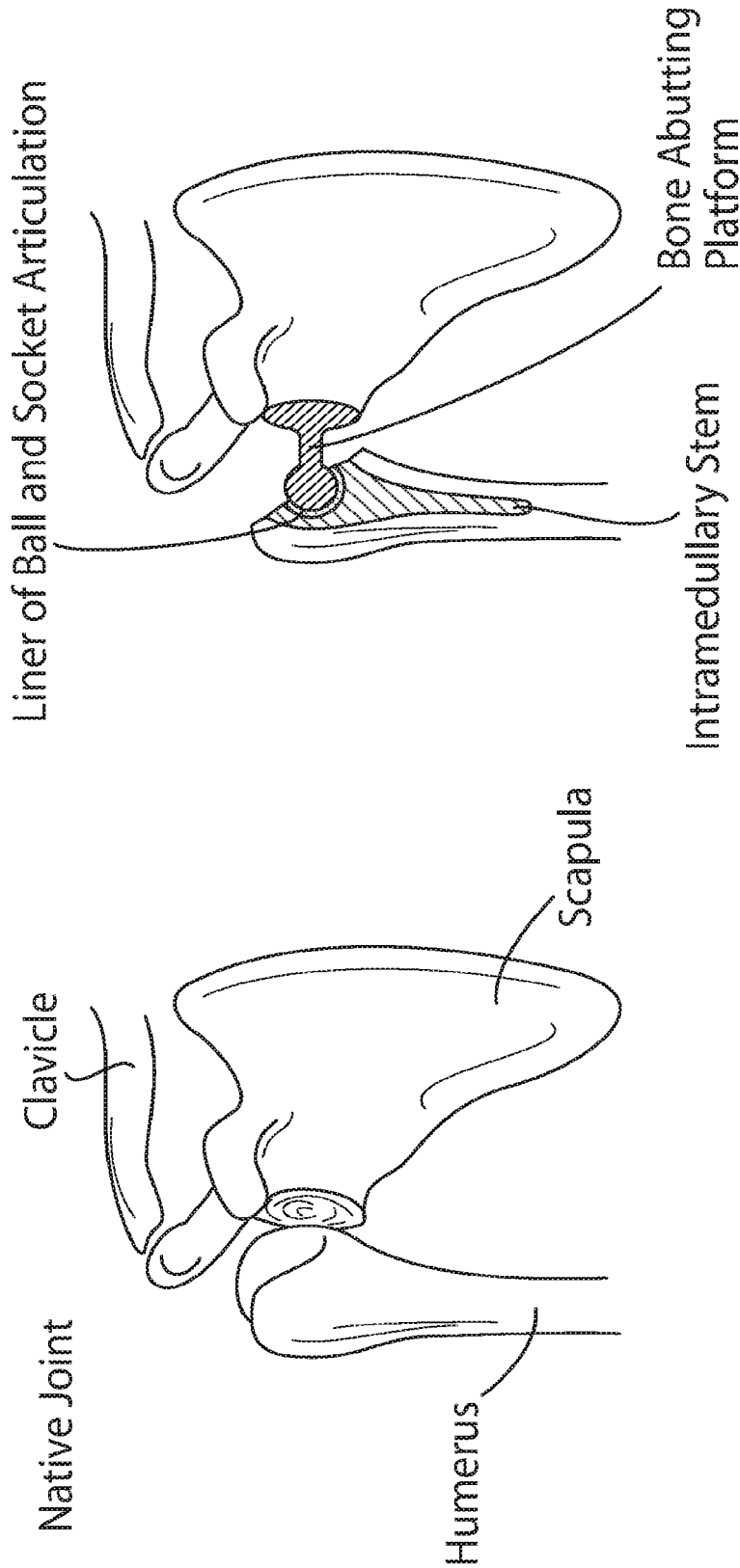

IMPLANT FOR A BONE JOINT

CROSS-REFERENCE TO RELATED APPLICATIONS

This application is a continuation of U.S. patent application Ser. No. 15/429,635, filed Feb. 10, 2017, which claims priority to European Patent Application No. 16155090.0, filed on Feb. 10, 2016, all of which are incorporated herein by reference in their entireties.

TECHNICAL FIELD

The invention relates to an implant for a bone joint, especially a carpometacarpal joint. In particular, the invention relates to a modular implant for a bone joint. The invention also relates to a kit of parts that can be assembled to form the bone joint implant of the invention. The invention also relates to a method of treating osteoarthritis or performing a hemi-arthroplasty by implanting a bone joint implant of the invention into a bone joint for the purpose of spacing articulating bones.

BACKGROUND TO THE INVENTION

Joint replacements may be generally divided into two designs—total arthroplasty and hemiarthroplasty. Total arthroplasty designs generally replace both sides of the joint, for example, a total hip replacement is made up of an acetabular cup which articulates with a femoral component comprising a ball and stem. A hemiarthroplasty generally only replaces one side of the joint. Using the hip again as an example, a hip hemiarthroplasty uses the native acetabular cup to articulate with a prosthetic ball and stem. Other examples include the shoulder where a total arthroplasty replaces both the humeral and scapular articular surfaces, while a hemiarthroplasty only replaces the articular surface of the humerus.

In some joints, with more complex biomechanics than the two ball and socket type joints mentioned above, both total and hemiarthroplasty designs have been used, with mixed success. An example of a joint with complex biomechanics is the first carpometacarpal joint of the thumb. This joint is made up of the trapezium bone, and the first metacarpal bone. During movements of this joint, the metacarpal bone moves in the following ways in relation to the trapezium; flexion and extension, abduction and adduction, internal rotation and external rotation. The metacarpal bone also translates across the trapezium bone. Movements of the thumb digit are enabled by a combination of any or all of these motions in different ratios depending on what motion is taking place.

As the movement of the thumb digit is determined by a combination of muscles activations, and in turn a combination of bony movements as described above, it has been found that the axis of rotation of the thumb is not always in the same place. The axis of rotation of the thumb joint moves depending on what movement of the thumb is taking place. The axis of rotation during abduction-adduction movements is in the base of the metacarpal, while the axis of rotation during flexion-extension is in the trapezium. In true terms, the axis of rotation of the joint shifts between these two points in line with the ratio of bone movements taking place.

While the saddle-shaped geometry of the CMC joint is largely responsible for the wide range-of-motion and functionality of the joint, the corresponding complex biomechanics are thought to be one of the primary causes of the high failure rate of both total arthroplasty and hemiarthroplasty implants which have been designed for this joint. This highly mobile joint may also predispose it to instability and osteoarthritis.

The other significant cause theorised as to the high failure rates of implants is the significant forces transmitted through the joint during forceful motions of the thumb, such as pinching, grasping or twisting. It has been shown that the forces transmitted through the CMC joint are up to ten times that exerted on the tip of the digit.

As all current total arthroplasty implants for the CMC joint require the implantation of one part in the trapezium, a common failure mechanism for this type of design is subsidence or failure of the trapezium element such as the cup and socket. By placing the socket in the trapezium, the point of rotation for all movements is now limited to one point, while it is known that the axis of rotation moves between the trapezium and the metacarpal in the native joint. The trapezium must also be surgically resected to allow placement of the cup and socket, decreasing the viable bone stock available. Therefore, by limiting the point of rotation to one position outside the natural shifting axis of rotation, placing this point in poor quality limited bone, and then subjecting this point of stress to multiplied forces of significant amounts, it is unsurprising that failure of the ball and socket element of total arthroplasty is a common failure mechanism.

Hemi-arthroplasty designs have been developed in an effort to avoid having to place the point of rotation in the trapezium, and instead, modify only the articular surface of the metacarpal. These designs have had limited success clinically, with no statistically significant difference in implant survival over total arthroplasties (Kurkhaug Y, Lie S A. Havelin L I, Hove L M. Hallan G. The results of 479 carpometacarpal joint replacements reported in the Norwegian Arthroplasty Register. Journal of Hand Surgery (E) 2014 39 (8): 819-825). As these hemiarthroplasty implants are uniblock i.e. one part designs, the forces applied to the implant from the trapezium as it moves tend to be transmitted to the stem of the implant. This has caused stem loosening and implant failures (Naidu S H, Kulkami N, Saunders M. Titanium Basal Joint Arthroplasty: A Finite Element Analysis and Clinical Study, The Journal of Hand Surgery. 2006 31(5)760-765). A uniblock hemi-arthroplasty device is described in U.S. Pat. No. 8,303,664.

Hemi-arthroplasty designs generally involve the modification or remodelling of the trapezium bone into a specific shape to accommodate the implant. This compromises the integrity of the trapezium bone. Another failure mode of hemiarthroplasty designs is luxation, i.e. dislocation of the implant from the surgically remodelled trapezium (Pritchett J W, Habryl L S. A Promising Thumb Basal Joint Hemiarthroplasty for Treatment of Trapeziometacarpal Osteoarthritis. Clinical Orthopaedics and Related Research. 2012; 470 (10):2756-2763; Martinez de Aragon J S. Early Outcomes of Pyrolytic Carbon Hemiarthroplasty for the Treatment of Trapezial-Metacarpal Arthritis Journal of Hand Surgery, Volume 34, Issue 2, 205-212).

Patents for two-part hemiarthroplasty devices have been noted, however, these designs require the dynamic reconfiguration of the two parts relative to each other to achieve an alteration in the point of motion. FR2912051 discloses such a device. While this device provides two articulation points, the two parts of the device need to be separated (dynamic reconfiguration) to achieve a movement of the axis of rotation (as shown in FIG. 4 of FR2912051). As any device implanted in this joint would be expected to be under physiological compressive forces of significant amounts, this dynamic reconfiguration would be impossible to achieve to a degree that would provide any meaningful biomechanical or clinical impact.

It is an object of the invention to overcome at least one of the above-referenced problems.

STATEMENTS OF INVENTION

The Applicants have overcome the problems of the prior art by providing a bone joint implant having a distal part configured for intramedullary engagement of a second bone, a proximal part configured for non-engaging abutment of an adjacent first bone, and an articulating coupling provided between the distal and proximal parts of the implant. The provision of an articulating coupling (for example a ball and socket) on the implant itself avoids the need to modify the first bone to provide for an articulating coupling between the bone and the implant and avoid the complications and failure rates associated with such designs. In addition, the configuration of the proximal part of the implant for non-engaging abutment with the first bone allows for a greater degree of articulation between the first and second bones, including translational movement of the second bone in relation to the first bone which can provide for flexion-extension articulation and the articulated coupling which can be optimised for provision of abduction-adduction articulation. Thus, the implant of the invention provides for two points of articulation, specifically translational abutment against first bone, and the articulated coupling between the proximal and distal ends of the implant, and both articulation points can function concurrently and independently without the need for dynamic reconfiguration of the implant. This provides a distinct advantage over the hemi-arthroplasty implant of the prior art (FR2912051) which requires dynamic reconfiguration (i.e. separation) of the two parts of the implant before the axis of rotation can be moved and which is unable to provide two points of articulation that can act concurrently and independently.

Accordingly, in a first aspect, the invention provides an implant for a mammalian bone joint for spacing a first bone of the joint from a second bone of the joint while allowing translational movement of the second bone in relation to the first bone, the implant comprising (a) a distal part configured for intramedullary engagement with an end of the second bone, (b) a proximal part configured for non-engaging abutment of an end of the first bone and at least partial translational movement thereon, and (c) an articulating coupling provided between the distal and proximal ends allowing controlled articulation of the first and second bones.

In one embodiment, the proximal part includes a bone-abutting platform shaped to conform to and translate upon the end of the first bone.

In one embodiment, the bone-abutting platform is shaped to conform to a natural shape of the end of the first bone. This avoids surgical resection of the end of the first bone, and allows the implant abut the end of the first bone while allowing the platform slide on the first bone.

In one embodiment, the end of the first bone is re-shaped, and the bone-abutting platform shaped to conform to and translate upon the re-shaped end of the first bone.

In one embodiment, the end/tip of the trapezium is resected to leave a flat surface and the bone-abutting platform is flat.

In one embodiment, the bone joint is a saddle joint.

In one embodiment, the saddle joint is a basal joint of the thumb, and in which the distal part is configured for intramedullary engagement with an end of the metacarpal and in which the proximal part is typically configured for non-engaging abutment of an end of the trapezium and at least partial translational movement thereon.

In one embodiment, the platform has a generally saddle-shape suitable for partially conforming to the shape of the end of the trapezium in the basal thumb joint.

In one embodiment, the articulating coupling is a ball and socket joint.

In one embodiment, the distal (or intermedullary) part comprises the ball and the proximal part comprises the socket.

In one embodiment, the distal part comprises the socket and the proximal part comprises the ball. In one embodiment, the socket is disposed within the distal part. In one embodiment, a mouth of the socket is substantially flush with a proximal end of the distal part. In one embodiment, the socket is defined by a socket liner which is disposed in an end of the distal (or intermedullary) part. In one embodiment, the socket is offset with respect to a longitudinal axis of the distal part. In one embodiment, the socket is offset with respect to a longitudinal axis of the distal part in a volar direction. In one embodiment, the ball and socket are configured for snap-fit engagement.

The implant is generally configured such that an articulating surface of the bone-abutting platform is sufficiently spaced from the articulating coupling to provide sufficient clearance to allow unhindered articulation of the metacarpal. In one embodiment, the bone abutting platform is spaced from the proximal part of the articulated coupling by a stem.

In one embodiment, the device is configured such that articulation of the articulated coupling (i.e. the ball and socket) and articulation of the bone-abutting platform can take place concurrently and independently without dynamic reconfiguration of the implant.

In one embodiment, the articulating surfaces of the ball and/or socket comprise a wear-resistant liner. Examples of suitable materials include Ultra High Molecular Weight High Density Polyethylene (UHMWHDPE); highly cross-linked Ultra High Molecular Weight Polyethylene (UHMWPE) and Nylon 12.

In one embodiment, the distal part and/or proximal part is configured for length adjustment to vary the spacing between the first and second bones.

In one embodiment, the proximal end comprises a bone abutting/engaging part, a coupling part and a spacer (ideally an adjustable spacer) between the bone abutting/engaging part and the coupling part.

In one embodiment, the (optionally adjustable) spacer comprises a stem that threadingly engages the bone abutting engaging part and is axially adjustable between an extended and retracted position.

In one embodiment, the stem is configured to extend axially away from the bone generally parallel to a longitudinal axis of the bone (i.e. second bone).

In one embodiment, the stem is configured to extend away from the bone at an oblique angle to the bone.

In one embodiment, the implant is a modular implant comprising a first component including the distal part and second component comprising the proximal part. This arrangement allows flexibility for the user to match distal parts with a suitable proximal part depending on the requirements of the patient, for example the spacing required, or different patient specific bone stock. It also allows provision of a kit comprising a number of different proximal and/or distal parts, having for example different spacing, different first bone abutting platforms, different articulating couplings, and different second bone intramedullary engagement.

In one embodiment, the first or second component comprises the articulating coupling.

In one embodiment, the first component comprises part of the articulating coupling and the second component comprises another part of the articulating coupling. An example of the latter is a ball and socket joint.

In one embodiment, the implant is a modular implant comprising three components:
a first component comprising the proximal part having a first bone-abutting platform at one end and one of a ball or socket at an opposite end; a second component comprising the distal part having one end configured for intramedullary engagement with the second bone; and a third spacer component having one of a ball and socket at one and an opposite end configured for engagement with the second component.

In one embodiment, the implant is a modular implant comprising three components: a first component comprising the proximal part having a first bone-abutting platform at one end; a second component comprising the distal part having one end configured for intramedullary engagement with the second bone and one of a ball or socket at an opposite end; and a third spacer component having one of a ball and socket at one and an opposite end configured for engagement with the second component.

In one embodiment, the distal part is configured for threaded intramedullary engagement with the second bone. Thus, an end of the distal part may include external threads to allow such engagement. Other intramedullary engagement means will be known to a person skilled in the art including compression fittings.

In one embodiment, the implant is a modular implant comprising an intramedullary engagement bolt for engagement with the second bone, a stem configured for engagement with the intramedullary bolt and having one part of an articulating coupling, and a platform configured for abutting an end of the first bone and translational movement thereon and having a second part of the articulating coupling.

In one embodiment, the stem comprises one of a ball and socket and the platform comprises the other of a ball and socket.

In one embodiment, the stem comprises a ball and the platform comprises a socket.

In one embodiment, the stem comprises a socket and the platform comprises a ball.

In one embodiment, the stem is configured for axial lengthening.

In one embodiment, the implant is a modular implant comprising an intramedullary engagement bolt for engagement with the second bone and having one part of an articulating coupling, a platform configured for abutting an end of the first bone and translational movement thereon, and a stem configured for engagement with the platform and having one part of an articulating coupling.

In one embodiment, the stem comprises one of a ball and socket and the platform comprises the other of a ball and socket.

In one embodiment, the stem comprises a ball and the platform comprises a socket.

In one embodiment, the ball or socket is disposed within the intramedullary engagement bolt.

The invention also provides a kit of parts which can be assembled to form a modular implant of the invention.

In one embodiment, the kit comprises a plurality of different first components and/or a plurality of different second components.

The invention also relates to a method of treating osteoarthritis of a bone joint in a subject having first and second bones comprising the steps of inserting an insert of the invention into the bone joint, in which the distal (or first or intermedullary) part of the insert configured for intramedullary engagement is inserted and anchored into a medullary cavity of the second bone and in which the proximal (or second or bone-abutting) part of the insert non-engagingly abuts the top of the first bone.

The invention also relates to a method of performing a hemi-arthroplasty on a bone joint in a subject having first and second bones comprising the steps of inserting an insert of the invention into the bone joint, in which the distal (or first or intermedullary) part of the insert configured for intramedullary engagement is inserted and anchored into a medullary cavity of the second bone and in which the proximal (or second or bone-abutting) part of the insert non-engagingly abuts an end of the first bone.

In one embodiment, the method comprises the steps of optionally separating the first and second bones (for example using a retractor), forming a medullary cavity in a proximal end of the second bone, inserting the distal part at least partly (and ideally fully) into the medullary cavity, attaching the proximal part to the distal part by means of the articulating coupling, and releasing the separation of the first and second bones. In one embodiment, the distal part is fully inserted into the medullary cavity. In one embodiment, a mouth of the socket is substantially flush with an end of the second bone. In one embodiment, the method includes an initial step of resecting an end of the second bone (ideally leaving a flat proximal end surface), prior to formation of the medullary cavity. In one embodiment, the distal part comprises an intermedullary interference fit stem, and in which the method includes a step of forcing the stem into an interference fit with the medullary cavity. In one embodiment, the medullary cavity is substantially parallel to a longitudinal axis of the bone. In one embodiment, the medullary cavity is substantially coaxial to a longitudinal axis of the bone. In one embodiment, the medullary cavity is offset at an angle to a longitudinal axis of the bone (for example 5-40°).

In one embodiment, the subject has osteoarthritis.

In one embodiment, the medullary cavity is formed in a distal end of the bone. In this embodiment, the insert is inserted into the joint through the joint capsule. The insert may be unassembled prior to insertion, with one of the parts being inserted prior to the insertion of the other part. For example, the distal part may be inserted into the capsule and inserted into the medullary cavity and secured by interference fit. Then the proximal part may be inserted and connected to the distal part and positioned abutting the first bone. The method generally involves a step of separating the first and second bones during the procedure.

In one embodiment, the medullary cavity comprises an elongated bore that extends longitudinally through the second bone from a distal end, typically to close to a proximal end. In one embodiment, the distal part of the insert comprises a stem configured for interference fit in the medullary cavity. In one embodiment, the stem tapers inwardly towards its distal end. In one embodiment, the medullar cavity is disposed towards a volar direction of the bone.

In one embodiment, the insert is inserted into the joint in an interosseous approach through the elongated bore in the second bone distal to proximal.

In one embodiment, the insert is inserted in an assembled form.

In embodiment, the joint is a first carpometacarpal joint, the subject has had a trapeziectomy, and the first bone is the scaphoid bone, wherein the platform of the proximal part is configured for non-engaging abutment of an end of a scaphoid bone. In one embodiment, the subject has had a trapeziectomy, and has a collapsed joint as a result of the trapeziectomy.

Other aspects and preferred embodiments of the invention are defined and described in the other claims set out below.

BRIEF DESCRIPTION OF THE FIGURES

FIG. 4A is an underneath plan view of the assembled insert of the invention;

FIG. 4B is a sectional view of the insert taken along the lines A-A of FIG. 4A;

FIG. 4C is a side elevational view of the trapezial base of FIG. 4:

FIG. 4D is a perspective view of the insert of FIG. 4C;

FIGS. 5A to 5I illustrate a method of performing a thumb basal joint hemi-arthroplasty according to the invention, employing an insert of the invention:

FIG. 6A illustrates the bones of the hand, and FIG. 6B illustrates the bones of the hand following a trapeziectomy (removal of the trapezium):

FIGS. 9A and 9B illustrate the use of an insert of the invention to perform a hemi-arthroplasty of the glenohumeral (shoulder) joint, where the insert comprises an intermedullary compression fitting with integrated socket configured for insertion into an optionally resected proximal end of the humerus, and a scapula base comprising a scapula abutting platform, platform neck and ball:

DETAILED DESCRIPTION OF THE INVENTION

Figure 1:
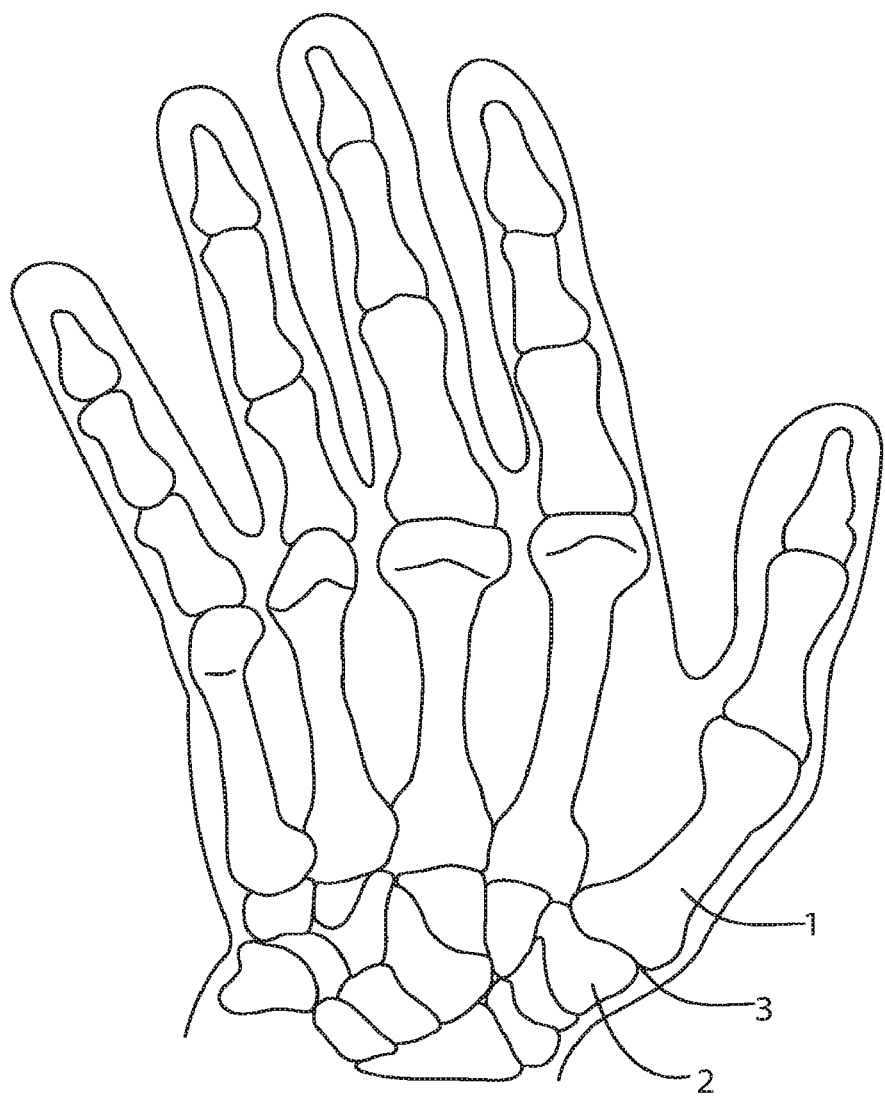
FIG. 1 is an illustration of the bones in the hand showing the carpometacarpal joint, metacarpal and trapezium bones.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes: and rodents such as mice, rats, hamsters and guinea pigs. In preferred embodiments, the subject is a human.

"Implant" means a prosthetic implant suitable for implantation in the body and made from a material or materials that are biocompatible (i.e. will not elicit an immune response in the host). Examples of suitable materials include Titanium, UHMWHDPE, Cobalt-Chrome alloy (CoCr), 316 grade Stainless Steel, Zirconium, Carbon-fiber-reinforced polyetheretherketone (CFR-PEEK), and Pyrocarbon. The implant comprises a distal part (also referred to as an "intermedullary part" or a "first part") and a proximal part (also referred to as a "bone-abutting part" or a "second part"). It should be noted that the distal part may be disposed on a proximal side of the joint (for example in the case of metatarsophalangeal joint illustrated in FIG. 15A below where the "distal part" of the implant is disposed on the proximal side of the joint).

"Mammalian bone joint" means one or more of the following: saddle joint (i.e thumb carpometacarpal joint), ball and socket joint (i.e. head of humerus and scapula joint or elbow humeroradial joint), hinge joint (i.e. interphalangeal joint in hand or foot, humeroulnar joint in elbow), pivot joint (i.e. radium ulna joint, intervertebral joint in spine, distal radioulnar joint in wrist), gliding joint (i.e. carpal bone in hand, acromioclavicular joint in shoulder, tarsometatarsal joint in foot), and condyloid joint (i.e. metacarpophalangeal joint in fingers, metatarsophalangeal joint in foot). In a preferred embodiment, the implant is configured for spacing articulating bones in a saddle joint. In a preferred embodiment, the implant is configured for spacing articulating bones in a carpometacarpal joint in the thumb. In one embodiment, the implant is configured for use with an arthritic bone joint. In one embodiment, the bone joint is one in which normal bone articulation includes translational movement of one bone in relation to the other bone. In one embodiment, the joint is an unnatural joint, for example a joint where one of the articulating bones has been removed, for example a first carpometacarpal joint in a subject that has undergone a trapeziectomy where the implant is placed between a first metcarpal and a scaphoid bone.

"Intramedullary engagement" means engagement within a medullary cavity formed or existing in the bone, where the cavity is generally but not exclusively formed along a longitudinal axis of the bone. In one embodiment, the intramedullary engagement fixture comprises a screw or nail or interference-fit stem, although other intramedullary fixtures are known. Typically, the screw is externally threaded. Intramedullary fixtures are sold by Smith & Nephew, Zimmer, Synthes and other suppliers. The engagement anchors the implant to the bone. In one embodiment, the medullary cavity is formed in a position that is offset towards a volar direction.

"Non-engaging abutment" means that the proximal part is not fixed to the first bone, but is configured to abut the end of the bone in a manner that allows translational movement thereof. How this is achieved depends on the joint being treated and the specific anatomy of the first bone. As an example, the when the joint is a carpometacarpal joint in the thumb, the end of the trapezium bone has a twisted saddle shape (see FIG. 2 of Turker et al, Indian J Plast Surg. 2011, 44(2): 308-316) and the platform is configured to rest upon this saddle and allow translational movement of the platform across the saddle. Thus, in this embodiment, the curved saddle-shaped platform typically has a concave-convex shape, which is explained below with reference to FIGS. 10A and 10F, and which has a concave curvature along a longitudinal aspect, and a convex curvature along a lateral aspect. This shape has been shown to provide an engagement that closely mimics the physiological situation and allows for natural flexion-extension articulation.

"Translational movement of the second bone in relation to the first bone" means non-pivoting movement of the second bone in relation to the first bone. This can also be described as sliding movement. An example is the involuntary translational movement of the metacarpal in relation to the trapezium in the thumb carpometacarpal joint, which contributes significantly to extension-flexion articulation of the thumb. The implant of the invention facilitates such translational movement by employing a proximal part that is configured to non-engagingly abut the first bone.

"Articulating coupling" means a coupling that allows articulation between the first and second parts of the implant. The specific type of coupling employed in the implant depends on the joint that is being treated with the implant, and in some cases the indication or severity of the indication. For example, when the implant is for treatment of an arthritic hinge joint, for example an elbow joint, the implant will generally comprise a hinge joint coupling. When the implant is for treatment of a saddle joint, for example a carpometacarpal joint, the implant will generally comprise a ball and socket joint or a universal joint. "Controlled articulation" means that the articulation is constrained to specific types of articulation.

"Abutting platform" means a base that abuts the end of the first bone (for example the end of the trapezium) so that translational (i.e. sliding) movement of the platform in relation to the end of the bone is allowed. The bone is not fixed to the platform. The platform may be configured to conform to a surface of the top of the bone. In one embodiment, the platform is shaped to mimic an end of the second bone, so as to allow the same range of movements as the natural healthy joint, including translational movement. In the case of the carpometacarpal joint, where the end of the first bone (trapezium) has a twisted saddle topography, the platform may be shaped to conform to the twisted saddle to allow one or more or all of the following range of movements of the first metacarpal in relation to the trapezium; flexion, extension, abduction, adduction, internal rotation, external rotation, opposition, circumduction and translation.

"Modular implant" means that the implant is formed in at least two parts, for example three parts or four parts, and one or more of the parts may be replaced with a substitute part. For example, an implant may employ a proximal part that has a shape specific to a particular type of bone, or a different proximal part that has a shape specific to a different type of bone. Or an implant may have a distal part that comprises a screw for intramedullary engagement of the second bone, or a different distal part that comprises a nail for intramedullary engagement. The provision of a modular implant design allows a user to mix and match the different components to provide an implant that is tailored for a specific clinical situation.

"Osteoarthritis" is a condition that occurs when the protective cartilage on the ends of bones wears down or degenerates causing bone rubbing on bone. It most commonly occurs in joints of the hands, knees, hips and spine. Common symptoms include pain, tenderness and stiffness in the joints. Other forms of joint degeneration for which this device may be used in therapy for example to provide pain relief or structural integrity include post-traumatic arthritis, rheumatoid arthritis, psoriatic arthritis, and other forms of sero-negative and sero-positive arthropathies.

"Hemi-arthroplasty implant" means an implant that is configured for use in joint replacement where only one side of the joint is replaced or modified. The implants of the invention are predominantly hemi-arthroplasty implants, as the first bone is generally modified to receive the intermedullary anchor (and optionally by resection), the second bone is generally not modified, as the platform is configured to abut and translate upon the natural shape of the second bone.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIG. 1 there is illustrated a human hand showing the bones of the hand including the first metacarpal 1 and trapezium 2 which abut at the carpometacarpal joint 3.

Referring to FIGS. 2 to 4, an insert 30 of the invention configured for implantation into a saddle joint of the thumb is described. The assembled implant 30 is shown in FIG. 4, the distal (intermedullary) part is shown in FIG. 2 and the proximal (trapezium-abutting) part is shown in FIG. 3.

Figure 2B:
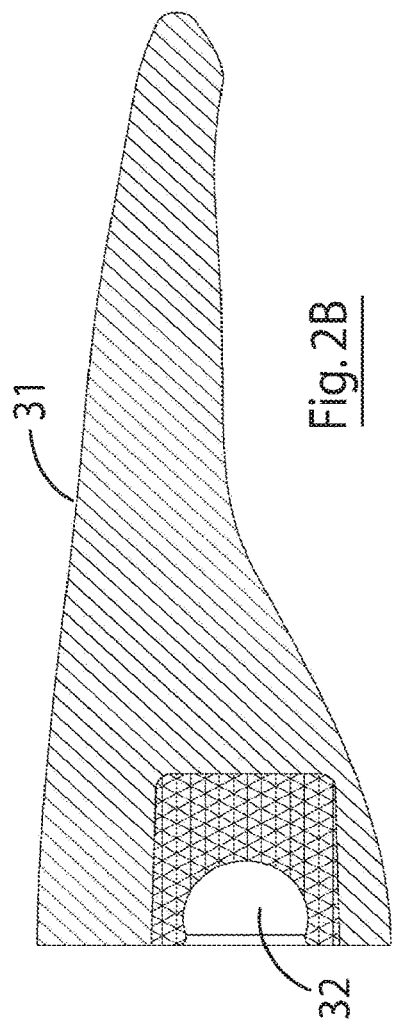
FIG. 2B is a sectional view of the metacarpal compression fitting taken along the lines A-A of FIG. 2A.
Figure 2C:
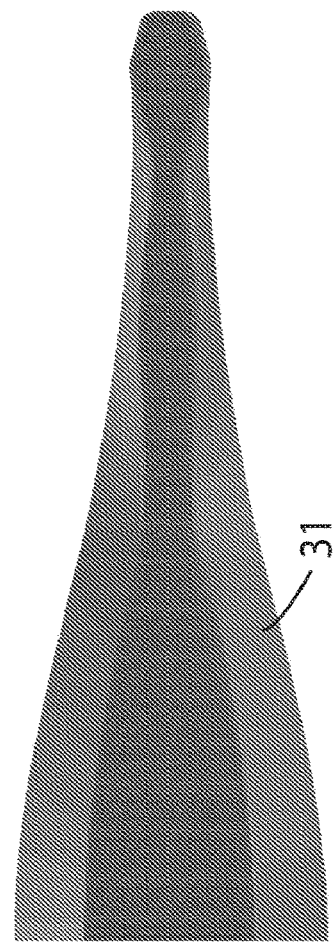
FIG. 2C is an elevational view of the metacarpal compression fitting of FIG. 2A.
Figure 2A:
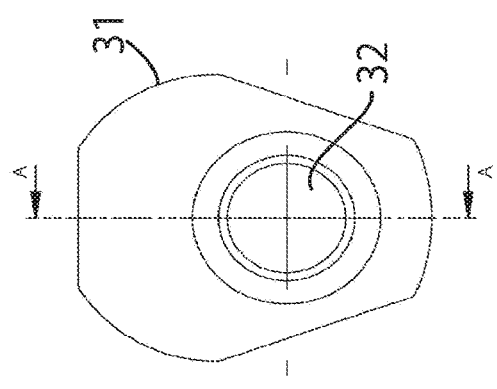
FIG. 2A is an end view of a proximal end of a metacarpal compression fitting forming part of an insert of the invention.
Figure 2D:
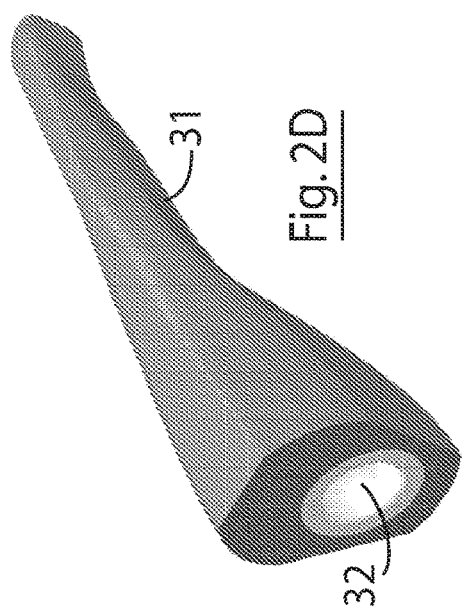
FIG. 2D is a perspective view of the metacarpal compression fitting of FIG. 2A showing the socket offset in a proximal end of the fitting in a volar direction.
Figure 3A:
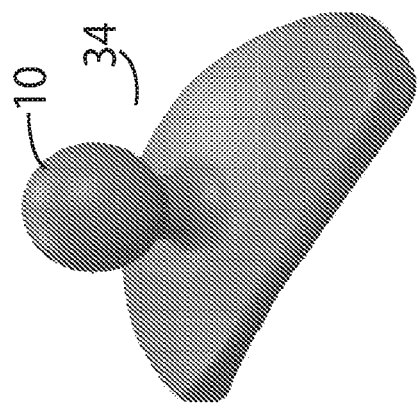
FIG. 3A is a sectional view of the trapezial base taken along the lines F-F of FIG. 3B.
Figure 3B:
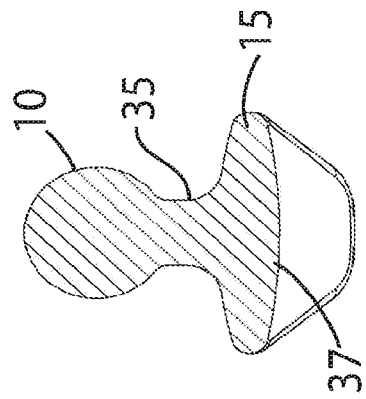
FIG. 3B is a top plan view of the trapezial base of FIG. 3C.
Figure 3D:
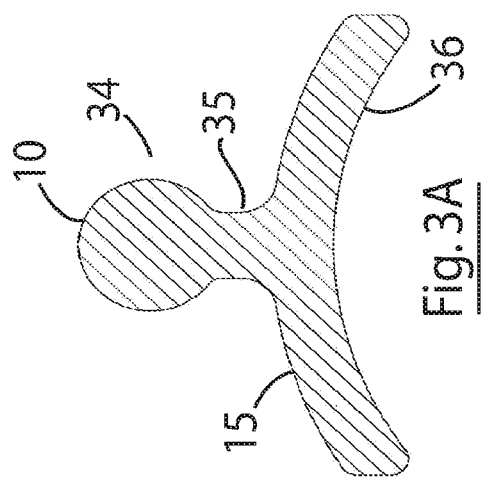
FIG. 3D is an end elevational view of the trapezial base of FIG. 3C.
Figure 3C:
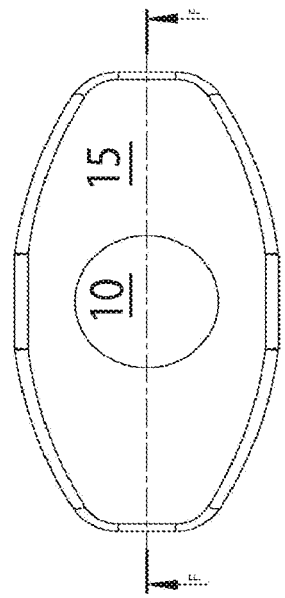
FIG. 3C is a perspective view of a trapezial base forming part of an insert of the invention.
Figure 3E:
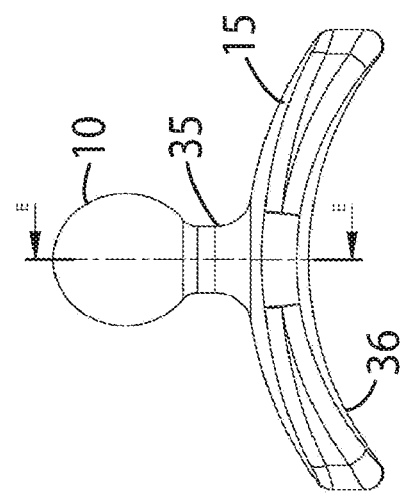
FIG. 3E is a side elevational view of the trapezial base of FIG. 3C.
Figure 3F:
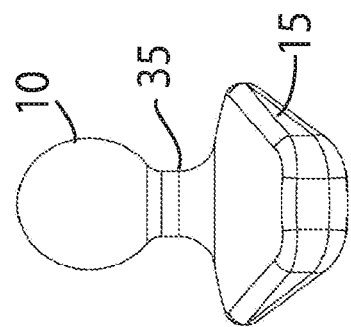
FIG. 3F is a sectional view of the trapezial base taken along the lines E-E of FIG. 3E.

FIGS. 2A to 2D illustrate the distal part of the insert—a metacarpal compression fitting 31 comprising an elongated stem 32 that tapers inwardly towards its distal end, and a socket liner defining a socket 32 inserted in a proximal end of the fitting 31 and offset in a volar direction. As shown in FIG. 2A, the proximal end of the fitting has a substantially frustoconical shape sectional shape, with the socket 32 disposed towards a narrowed end of the fitting, which in use is disposed towards the volar direction of movement of the metacarpal. FIGS. 3A to 3F illustrate the proximal part of the insert—the trapezial base 34 comprising a saddle-shaped platform 15 and ball 10 connected by a platform neck 35. The platform has curvature in two directions; a first concave curvature 36 along a longitudinal aspect of the platform 15 is illustrated in FIGS. 3A and 3F; and a second convex curvature 37 along a transverse aspect of the platform is illustrated in FIG. 2F. This dual curvature of the platform allows the platform to conform to the natural "twisted saddle" shape of the distal end of the trapezium bone and facilitate smooth translational movement thereon. FIGS. 4A to 4D show the inset 30 in an assembled form, with the ball of the trapezial base 34 inserted into the socket of the metacarpal compression fitting. It will be noted from FIGS. 4B and 4D that the platform neck 35 provides sufficient spacing between the platform and ball and socket to allow both points of articulation (ball and socket, and platform on trapezium) function concurrently and independently.

Figure 5A:
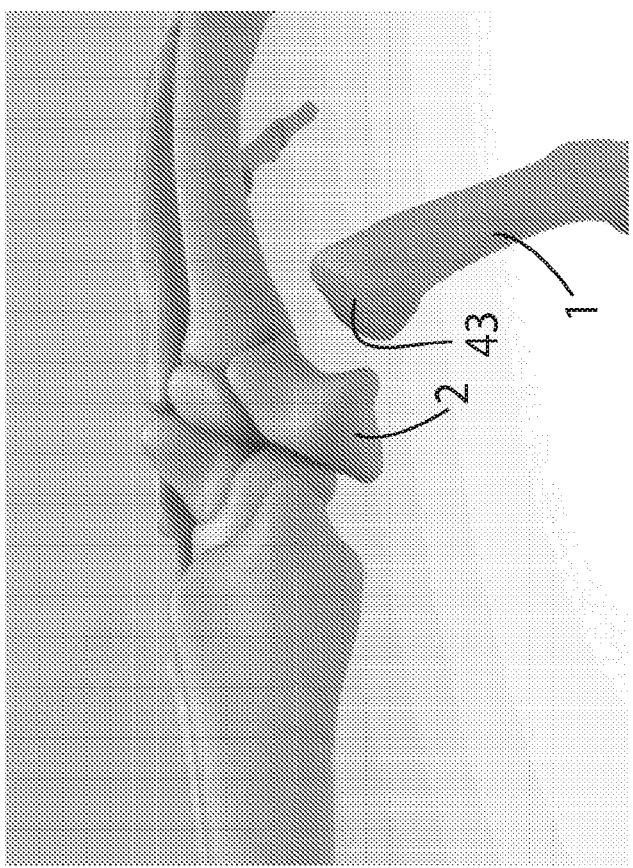
Figure 5B:
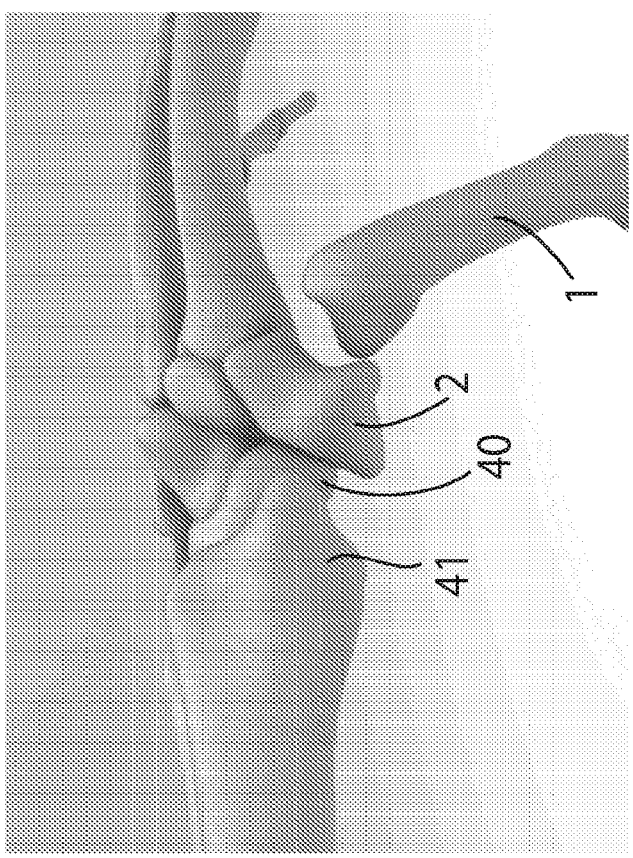
Figure 5C:
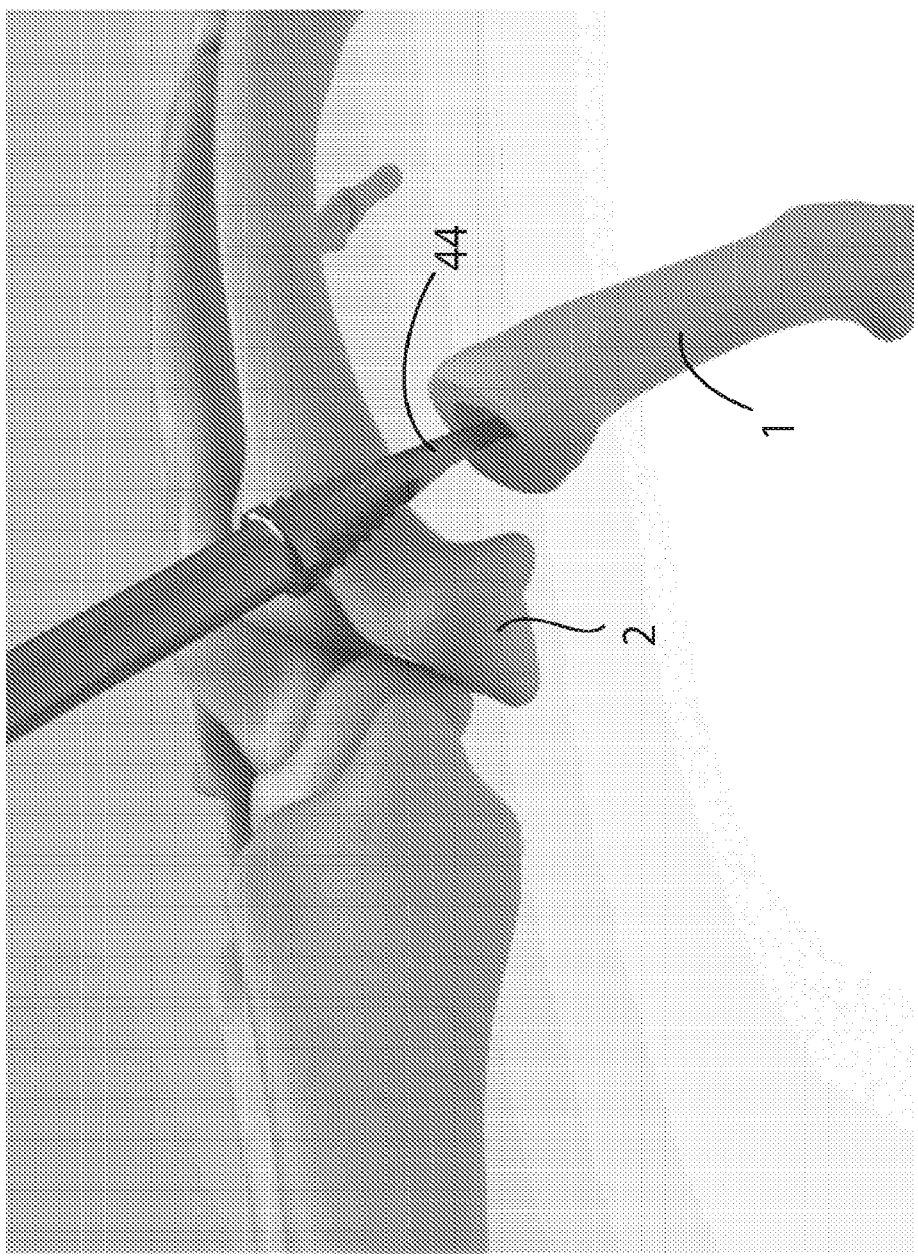
Figure 5D:
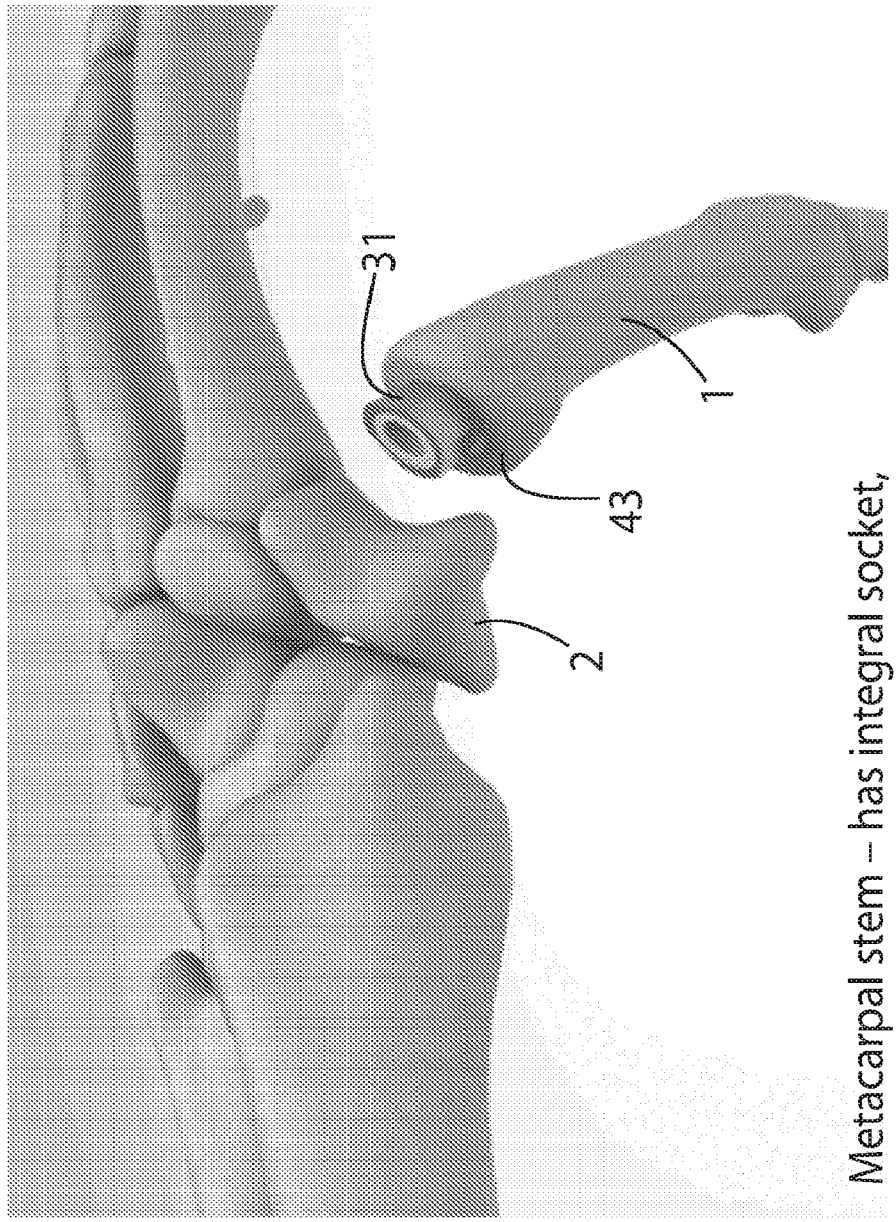
Figure 5E:
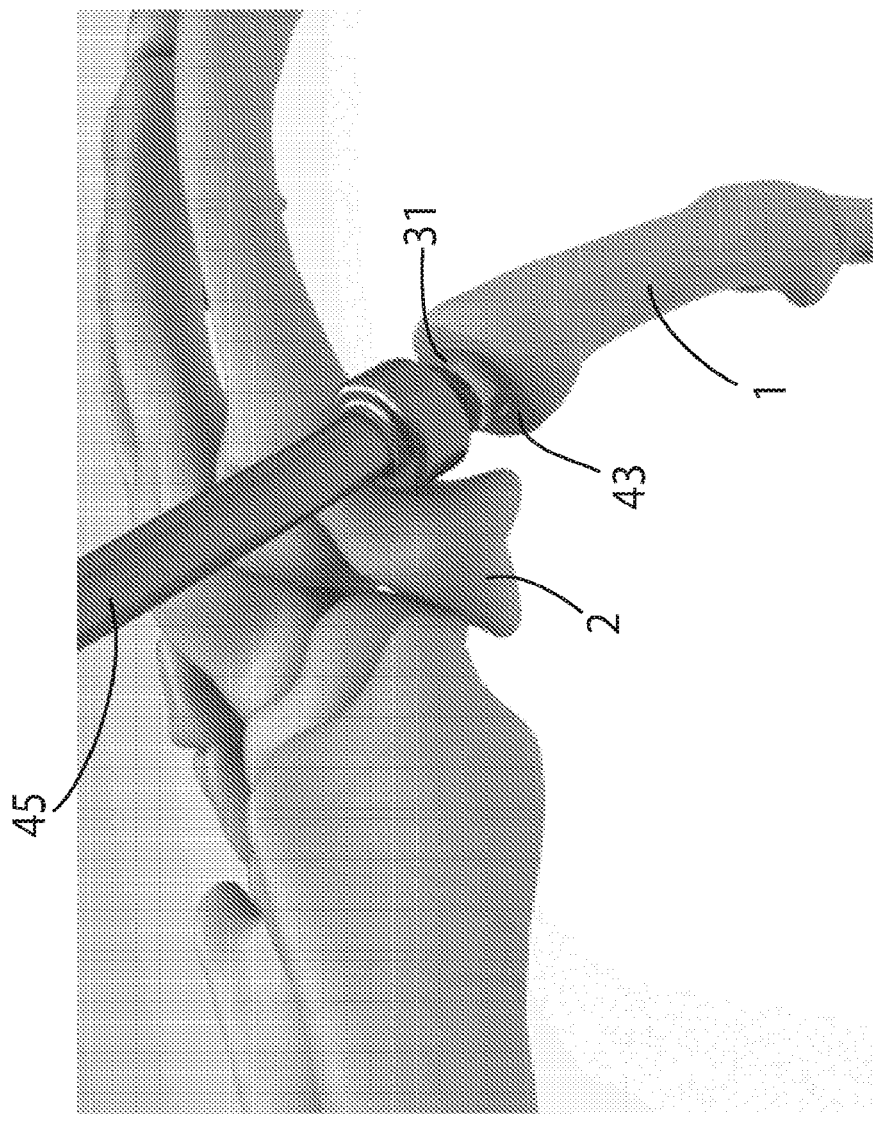
Figure 5F:
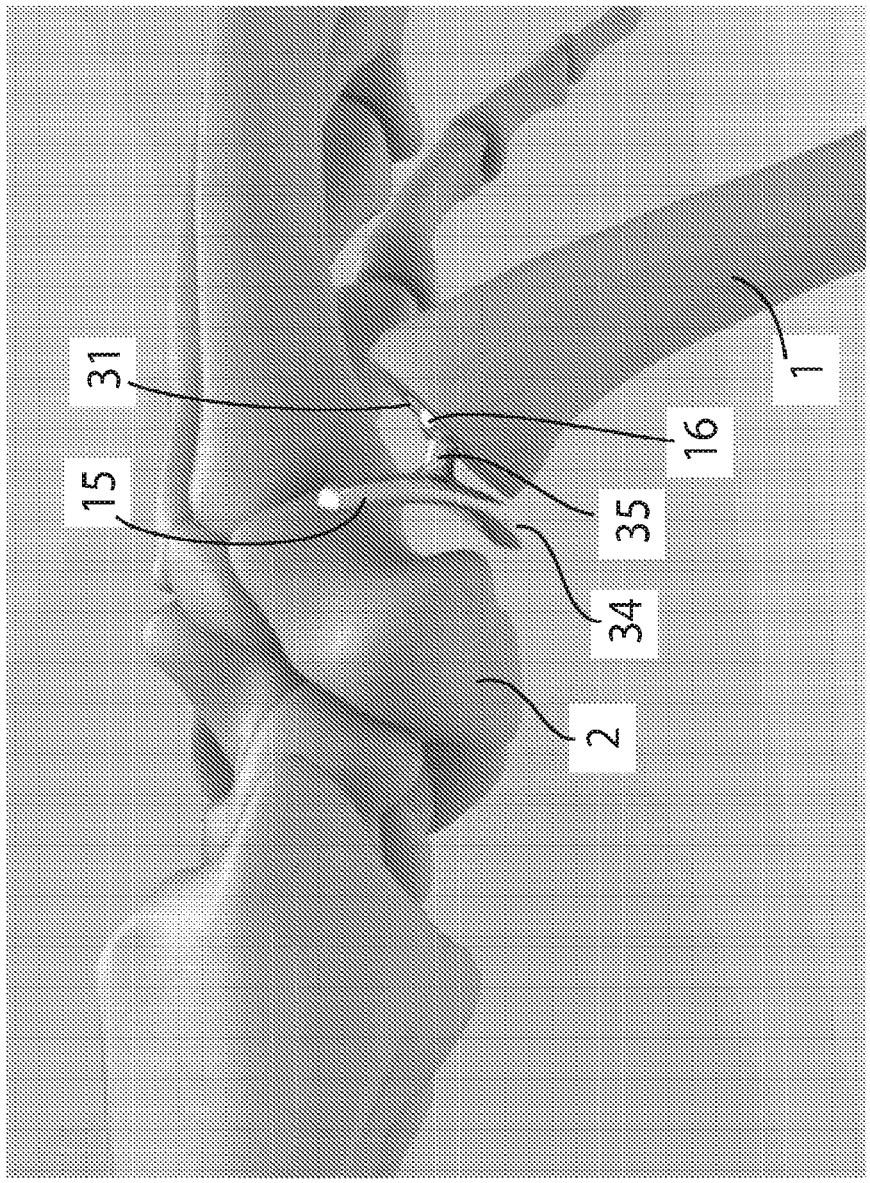
Figure 5G:
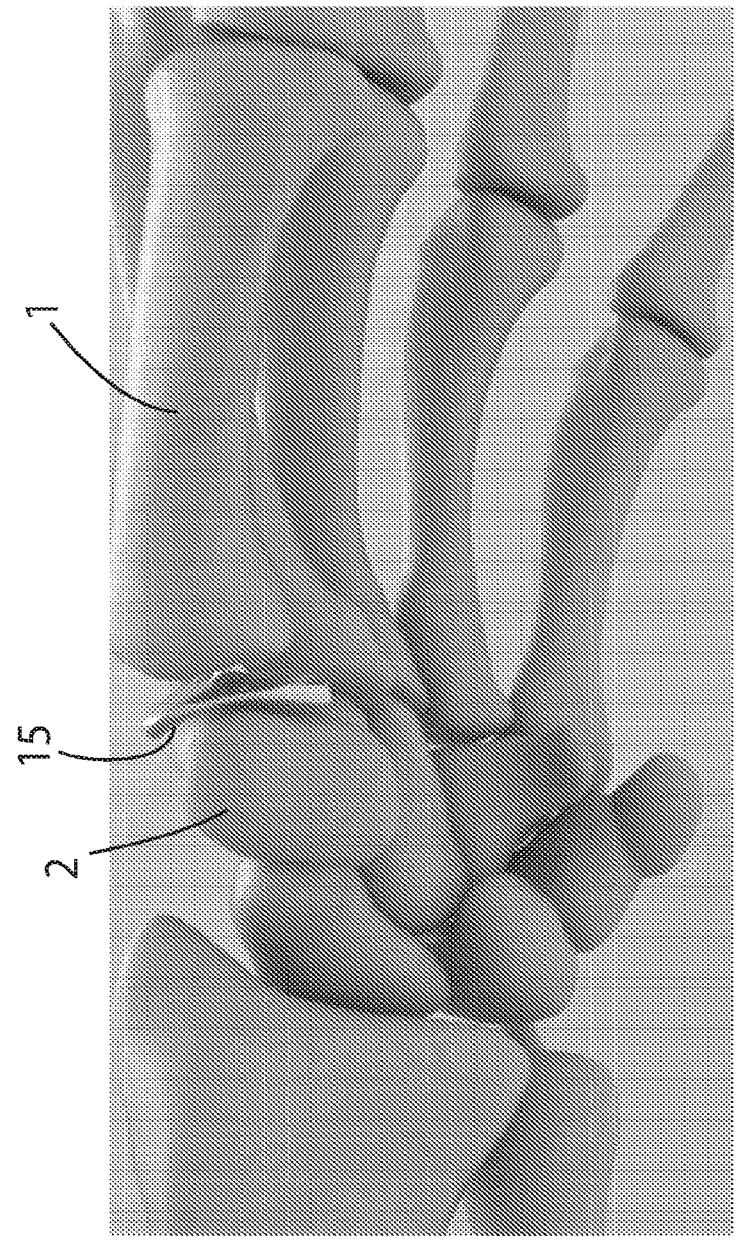

Referring to FIGS. 5A to 5G, a method of performing a basal thumb joint hemi-arthroplasty according to the invention, and employing an insert of the invention, is illustrated. Referring initially to FIG. 5A, the bones of the hand and fingers are illustrated including the first metacarpal 1, trapezium 2, scaphoid 40, and radius 41. A first part of the procedure as illustrated in FIG. 5B is surgical resection of a proximal end of the metacarpal, providing a flat proximal end 43 of the metacarpal 42. Referring to FIG. 5C, a broach 44 is employed to hollow out a medullary cavity in the metacarpal and form a placement position for the metacarpal compression fitting. The placement position is formed in a centre of the flat proximal end 43. Referring to FIG. 5D, the metacarpal compression fitting 31 is inserted into the placement position in the metacarpal, and an insertion tool 45 is employed to force the fitting 31 fully into the placement position by means of an interference fit leaving the proximal end of the fitting 31 (and mouth of the socket 32) flush with the flat proximal end 43 of the metacarpal. Referring to FIGS. 5F and 5G, once fitted securely into position, the trapezial base 34 is coupled to the metacarpal compression fitting 31 by means of the ball 16 on the trapezial base 34 and the socket 32 disposed in a proximal end of the fitting 31. The saddle based platform 15 of the trapezial base 34 is shaped with dual concave-convex curvature (as detailed above) to allow it conform to the shape of the distal end of the trapezium, and allow abutment between the trapezium and platform and simultaneous translational movement of the platform on the end of the trapezium, mimicking the physiological situation. The ball and socket connection allows rotational articulation of the metacarpal with respect to the platform, and the spacing between the (a) ball and socket articulation point and (b) the trapezium/platform articulation point allows both articulations to occur simultaneously and independently, without any requirement for the spacing between the bones to be altered, again mimicking the physiological situation. FIGS. 5H and 5I illustrate the operation of the insert of the invention, showing the alteration in position of the trapezial base in response to movement of the metacarpal. In use, articulation of the insert occurs preferentially at the ball and socket during abduction-adduction of the metacarpal, and preferentially at the trapezial base during extension-flexion. The insert does not have to reconfigure in size or shape to accommodate different movements.

Although all of the figures and specific embodiments relate to an implant configured for use with a carpometacarpal joint, it will be appreciated that the implant of the invention can be easily adapted for use with other types of saddle joint and other types of non-saddle joints, such as hinge joints, ball-and-socket joint, and sliding joints, for example. It addition, it will be appreciated that while the specific embodiment describes an implant having a ball and socket coupling, other types of couplings may be employed such as for example a universal joint or a hinge joint.

Figure 7A:
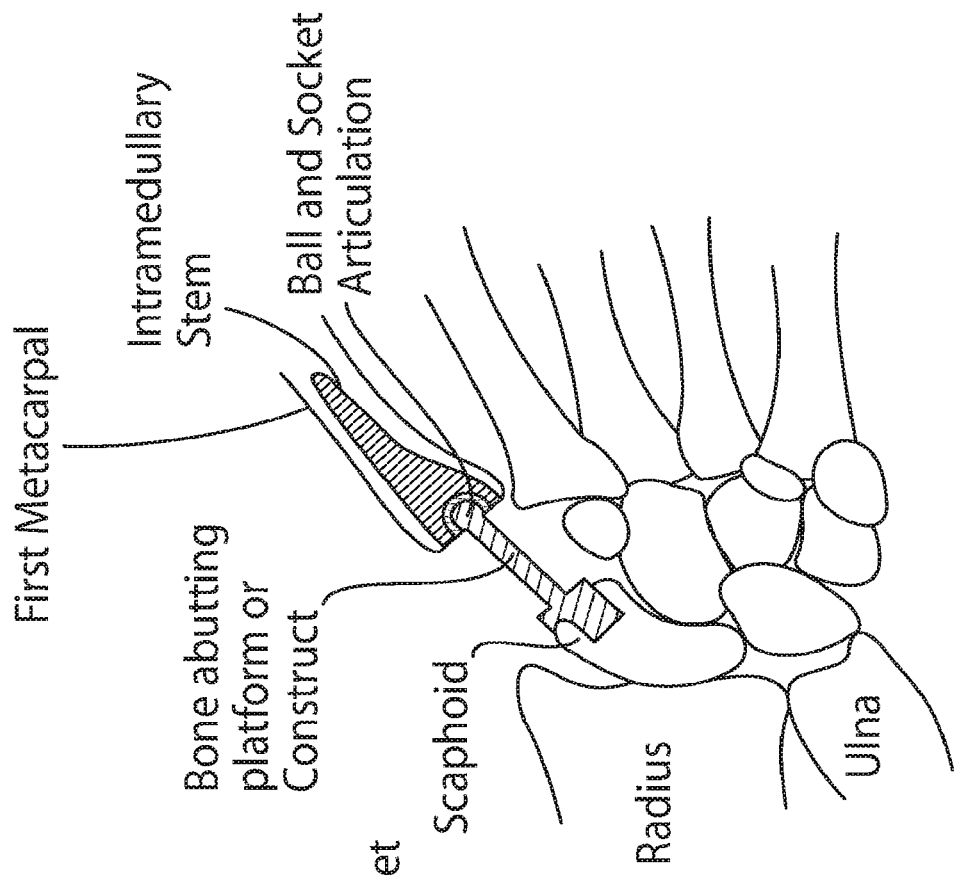
FIGS. 7A and 7B illustrate the use of an insert of the invention to perform a total arthroplasty of the basal thumb joint, where the trapezium is removed and the proximal part of the insert is configured to conform to the shape of, and abut, a distal end of the scaphoid bone.
Figure 7B:
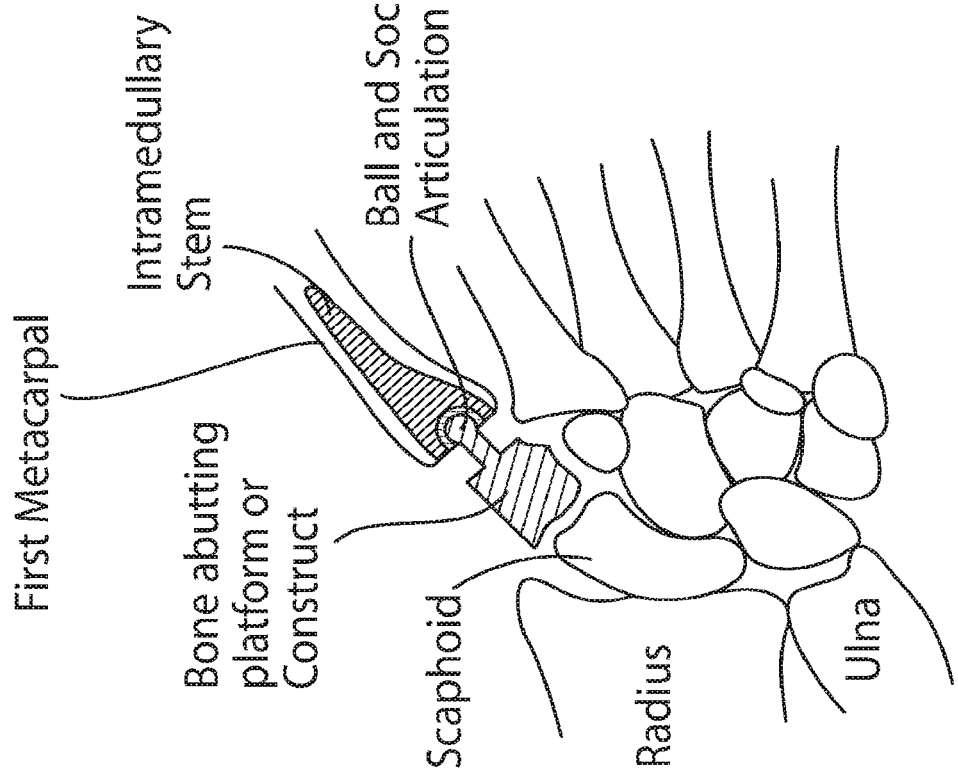

Referring to FIGS. 6 and 7, the use of an implant of the invention to perform an arthroplasty of the thumb basal joint is illustrated. FIG. 6A illustrates the bones of the hand, and FIG. 6B illustrates the bones of the hand following a trapeziectomy (removal of the trapezium). FIGS. 7A and 7B illustrate the use of an insert of the invention to perform a total arthroplasty of the basal thumb joint, where the trapezium is removed and the proximal part of the insert is configured to conform to the shape of, and abut, a distal end of the scaphoid bone. Two embodiments are illustrated, a first in which the planform is configured to abut only the scaphoid bone (FIG. 7A), and a second in which the platform is configured to abut the scaphoid bone and an adjacent bone (FIG. 7B).

Figure 8B:
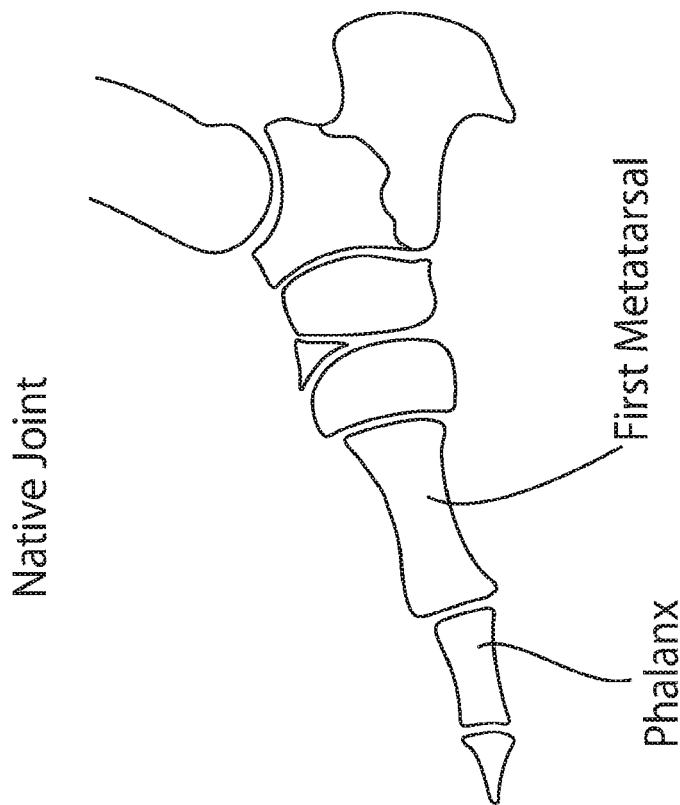
FIGS. 8A and 8B illustrate the use of an insert of the invention to perform a hemi-arthroplasty of the first metatarsophalangeal joint, where the insert comprises an intermedullary compression fitting with integrated socket configured for insertion into an optionally resected end of the first metatarsal, and a phalanx base comprising a phalanx abutting platform, stem and ball.
Figure 8A:
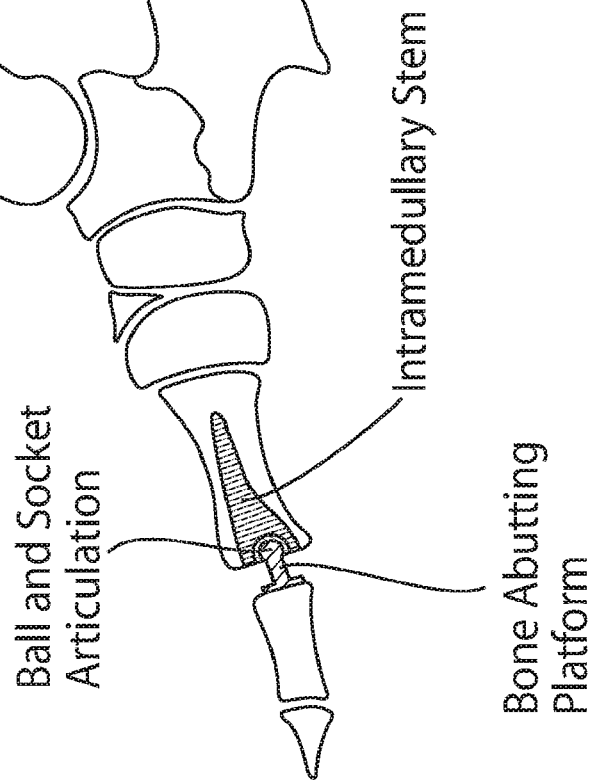

FIGS. 8A and 8B illustrate the use of an insert of the invention to perform a hemi-arthroplasty of the first metatarsophalangeal joint, where the insert comprises an intermedullary compression fitting with integrated socket configured for insertion into an optionally resected end of the first metatarsal, and a phalanx base comprising a phalanx abutting platform, platform neck and ball. In this embodiment, the intermedullary insert is configured for insertion into the first metatarsal as the phalanx is too small to accommodate an intermedullary stem.

FIGS. 9A and 9B illustrate the use of an insert of the invention to perform a hemi-arthroplasty of the glenohumeral (shoulder) joint, where the insert comprises an intermedullary compression fitting with integrated socket configured for insertion into an optionally resected proximal end of the humerus, and a scapula base comprising a scapula abutting platform, stem and ball.

Figure 10:
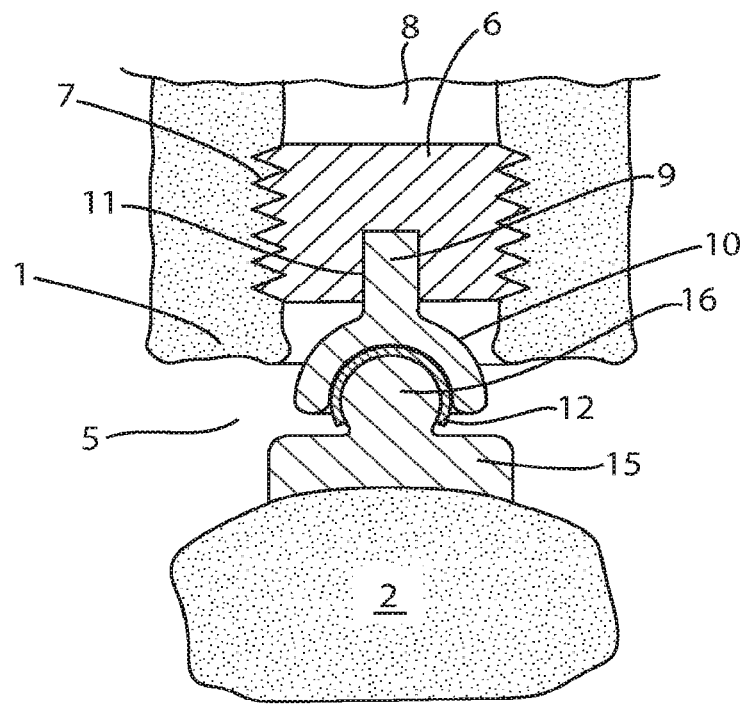
FIG. 10 is an illustration of an implant according to an alternative embodiment of the invention shown in-situ in a carpometacarpal joint.

Referring to FIG. 10 there is illustrated an insert according to another embodiment of the invention indicated generally by the reference numeral 5 and shown in-situ in a carpometacarpal joint 3 spacing the metacarpal bone 1 from the trapezium 2. In more detail, the insert 5 comprises a distal part and a proximal part. The distal part comprises an intramedullary screw 6 having external threads 7 for engagement with the medullary cavity 8 and a stem 9 bearing a socket 10, which houses a wear-resistant UHMWHDPE liner 12. The intramedullary screw includes a threaded bore 11 for receipt of the stem 9, whereby the effective length of the stem, and spacing distance, can be modified by rotation of the stem clockwise or counter-clockwise as required. The proximal part comprises a platform 15 an underside of which is shaped to conform to the saddle shape of the top of the trapezium, and a ball 16 configured for a constrained engagement with the socket 10. This embodiment of the insert of the invention is provided in modular form, in essentially four parts, screw, stem/socket, wear-resistant liner, and ball/platform. It is generally assembled prior to insertion into the joint by means of interosseous insertion through the medullary cavity which in this embodiment extends through the metacarpal (distal to proximal)—see "closed procedure" below. In this embodiment, the proximal part and platform are dimensioned to fit through the bore in the metacarpal.

Figure 11:
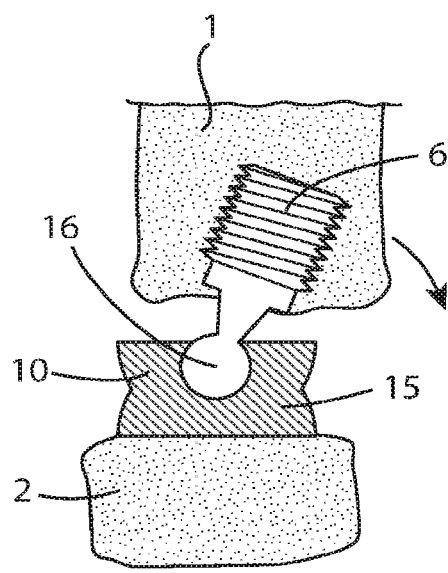
FIG. 11 is an illustration of an implant according to an alternative embodiment of the invention shown in-situ in a carpometacarpal joint.
Figure 12:
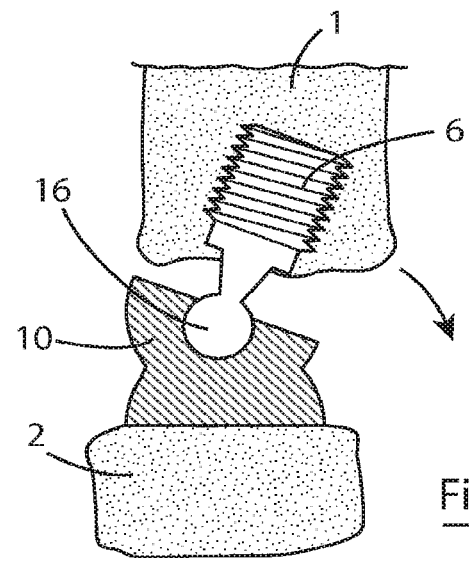
FIG. 12 is an illustration of an implant according to an alternative embodiment of the invention shown in-situ in a carpometacarpal joint.

Referring to FIG. 11, there is illustrated an alternative embodiment of the implant of the invention in which parts identified with reference to the previous embodiment are assigned the same reference numerals. In this embodiment, the medullary cavity is formed in the proximal end of the metacarpal 1, the ball 16 is provided on the distal part of the insert and the socket 10 is provided on the proximal part of the insert (it is formed as a recess in the distal part). In addition, the medullary cavity shown in FIG. 11 is not parallel with the longitudinal axis of the bone (as is the case with the embodiment of FIG. 10), but projects into the bone at an angle to the longitudinal axis of the metacarpal. This can create the possibility of a pinch-point when the thumb moves. If this occurs, it is possible to offset the socket 10 slightly, as shown in FIG. 12, which avoids risk of a pinch point and optimises the range of motion.

Figure 13:
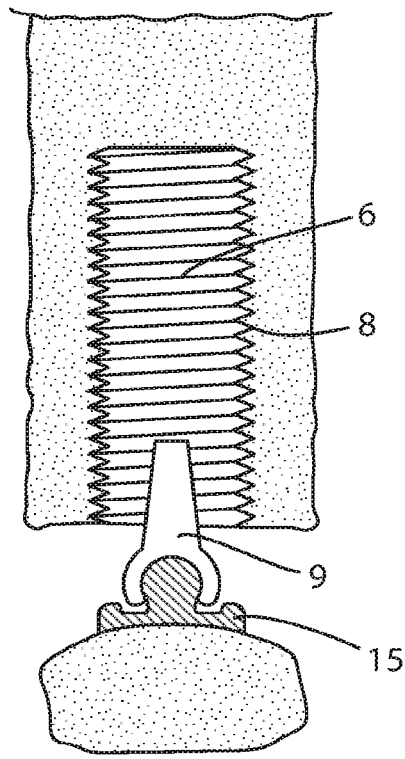
FIG. 13 is an illustration of an implant according to an alternative embodiment of the invention shown in-situ in a carpometacarpal joint.

Referring to FIG. 13, there is illustrated an alternative embodiment of the implant of the invention in which parts identified with reference to the previous embodiment are assigned the same reference numerals. This embodiment is similar to that of FIG. 10 with the exception that the medullary cavity 8 is formed in the proximal end of the metacarpal 1 and dimensioned to receive the intramedullary screw 6, and the platform 15 of the proximal part is wider providing for a greater area of abutment with the top of the trapezium. In addition, the periphery of the upper side of the platform has a lip which provides a volar and dorsal capture element which act to restrain excessive translational movement of the platform 15 on the top of the trapezium.

Figure 14:
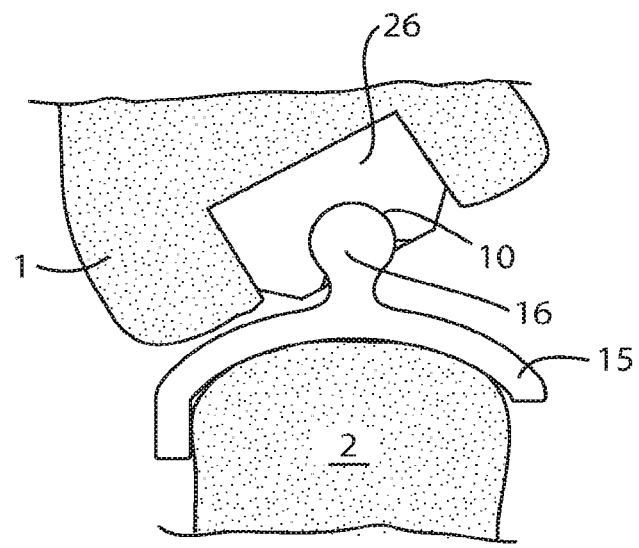
FIG. 14 is an illustration of an implant according to an alternative embodiment of the invention shown in-situ in a carpometacarpal joint.

Referring to FIG. 14, there is illustrated an alternative embodiment of the implant of the invention and in which parts identified with reference to the previous embodiment are assigned the same reference numerals. In this embodiment, am intramedullary compression fitting 26 in fixed into a medullary cavity formed in the proximal end of the metacarpal 1, and the socket recess 10 is formed in the compression fitting for receipt of the ball 16 such that the centre of the ball is located distal to the end of the metacarpal, which helps tighten the joint capsule ligaments and provide more stability in the joints. The intramedullary compression fitting 26 has an inwardly tapering shoulder 27.

Figure 15A:
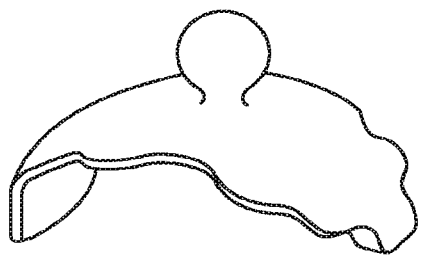
FIGS. 15A and 15B are illustrations of a proximal part of the implant of FIG. 6.
Figure 15B:
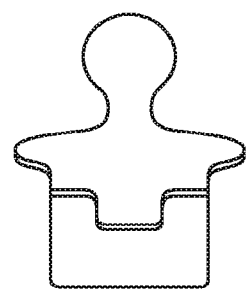

FIGS. 15A and 15B are detailed views of the proximal part of the implant of FIG. 14 showing the curved, saddle-shaped, platform 15 and ball 10.

Figure 16A:
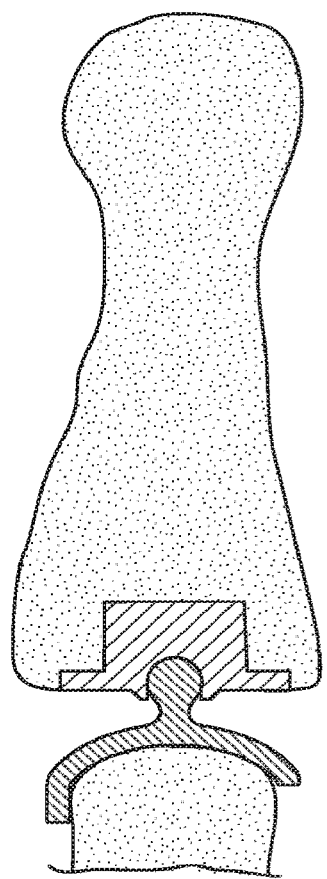
FIG. 16A is an illustration of an implant according to an alternative embodiment of the invention shown in-situ in a carpometacarpal joint.
Figure 16B:
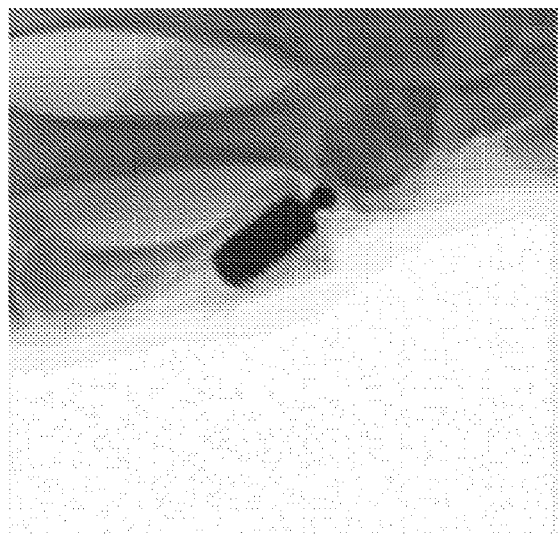
FIGS. 16B and 16C are X-ray images of an implant of the invention in-situ in the carpometacarpal joint of a human.
Figure 16C:
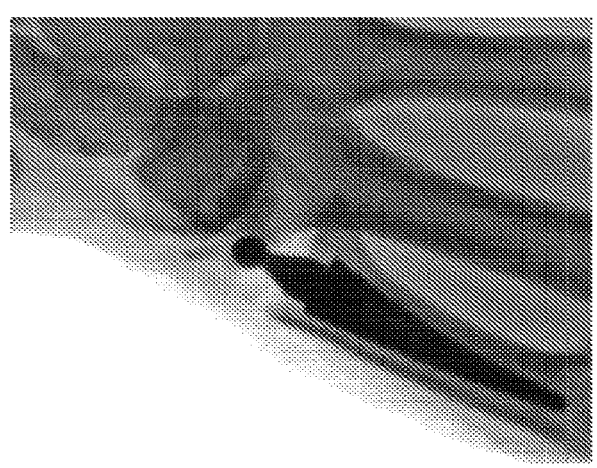

Referring to FIG. 16, there is illustrated an alternative embodiment of the implant of the invention and in which parts identified with reference to the previous embodiment are assigned the same reference numerals. In this embodiment, which is very similar to that of FIG. 14, the intramedullary compression fitting 26 is shouldered to provide a greater surface area to withstand migration of the device under compressive forces.

In one embodiment, the implant consists of two principal components, one male and one female. One component is typically fixed in the first metacarpal of the thumb—the metacarpal component and the second component is typically in contact with, and can translate upon, the trapezium—the trapezial component. Both principal components are generally connected to each other by means of a constrained ball and socket arrangement, and the female socket may be located on either the metacarpal or the trapezial side of the assembly.

The two principal components may be expanded to four (1), whereby the female socket component is fitted with a wear resistant liner, and a neck component comprising the ball is fitted into a housing to complete the male element of the design. The neck component may instead house the socket while the ball is integral with the translating trapezial component. The device may be presented in a range of sizes to suit a range of patient anatomy: this may be accomplished through providing a range of sizes for both metacarpal and trapezial components and a range of neck lengths. Similarly, necks may be straight or offset to compensate for individual anatomical variances, and sockets may also be offset (FIGS. 11, 12) to provide the widest range of motion. It is also possible to vary) the amount of joint distraction by having the neck component finely threaded and providing a means of axial adjustment relative to its housing.

Three specific embodiments are described below:

a. "Closed Procedure": An interosseous approach whereby the metacarpal component and the trapezial component are connected together before insertion. The socket feature may be located on either component. The components may be manufactured from commonly used orthopaedic materials provided that metal on metal contact is avoided and the trapezial component is made from a material that is compatible with articulation directly on bone. For example, the metacarpal component may be made from Titanium and the trapezial component may be made from UHMWHDPE.

A guide or guide wire such as a Kirschner wire may be inserted into the metacarpal on the lateral border extending proximally to exit at the centre of the articular surface. A series of pre-drilling then prepares an opportunity to either tap threads for, or insert a self-tapping version of, the metacarpal component. The threads may be of buttress design, have a slow helix and may be truncated to aid osteo-integration. Similarly, the metacarpal component may be fenestrated and/or coated with a material such as hydroxlyapatite to aid osteo-integration. As it is pre-attached, the trapezial component, which is just smaller than the root diameter of the metacarpal threads, precedes the metacarpal component down the channel until it rests upon the surface of the trapezium. The undersurface of the trapezial component may be flat, of generic saddle shape, or may be configured to mate with the superior surface of the trapezium and may or may not be patient specific in this regard. This patient specificity may be accomplished by using visual imaging techniques in conjunction with additive manufacturing, CNC fabrication or other computer aided manufacturing techniques. The trapezial component is not attached to the trapezium but is designed for translation upon the superior surface of the trapezium. Once in contact with the trapezium and (if not flat) oriented to the correct position relative to the saddle of the trapezium aided by external imaging, the assembly may be advanced by manipulation of the proximal end of the metacarpal component to provide the chosen degree of joint distraction.

In this embodiment, a drill guide may be used to aid initial position of the K-wire and a succession of pre-drills may be made with cannulated drill bits before the metacarpal components is inserted.

b. "Open Procedure": The metacarpal component may consist of a press-fit tapered stem inserted as an interference fit from the articular surface extending distally once the joint capsule has been exposed. Equally, the metacarpal component may be threaded into the articular surface of the metacarpal and may be of conical or some other shape that would aid retention and combat compression forces acting on the metacarpal. The trapezial component is larger than that of "a" above, and the underside of it may be flat to mate with a resected trapezium. Note that the amount of trapezial resection chosen may vary widely and none may be required based on individual patient anatomy.

In addition to being flat, the underside of the trapezial component may be of generic saddle shape or of a geometry that is patient specific and the top surface of the trapezial component may be shaped such that it is scalloped to better accommodate the native anatomy of the trapezium bone. The longitudinal edges of the trapezial component may be extended to provide both volar and dorsal capture elements which act to restrain excessive translation.

It may advantageous to utilise the embodiment of locating the ball on the trapezial component and by means of piloted counter boring, locate the centre of the ball distal to the resected end of the metacarpal. The effect of this countersunk placement may tighten the capsule ligaments and provide more stability to the joint. Note also that the metacarpal socket component may be shouldered such that a greater surface area is present to withstand migration of the device under compressive force.

c. "Semi-open Procedure": In this configuration, the metacarpal component is threaded and is introduced in the manner of "a" above, while the trapezial component is introduced via a smaller incision than with "b" above. The trapezial component will be larger than that of "a" and may or may not be patient specific.

In circumstances whereby an elliptical aperture remains at the external surface of the metacarpal due to a metacarpal component insertion at an angle to the long axis of the metacarpal, the aperture may be filled with osteogenative material such as bone graft or some other orthobiologic agent. The same applies to screws with fenestration or truncated thread forms.

Post insertion, the patient may be cast or splinted for an adequate time to enable osteo-integration.

Application of the Invention

The device may be used in locations throughout the musculoskeletal system other than the carpometacarpal (CMC) joint, although the CMC joint is the area of focus in the device description below.

Other joints where the device in suitably modified form may be considered include: Small joints of the hand: Interphalangeal, Metacarpophalangeal and Scaphotrapezial joints Wrist: Radiocarpal and Distal radioulnar joint Shoulder: Acromioclavicular joint Ankle: Talotibial joint—central, medial and lateral surfaces.

Foot: Metatarsophalangeal, Tarsometatarsal, Naviculocuneiform and Interphalangeal joints Elbow: Humeroulnar, Humeroradial and Superior radioulnar joints Spine: Intravertebral or Sacroiliac and Facet joints Advantages of One Preferred Embodiment The trapezium bone does not need to be remodelled for the device to function. A surgeon may undertake some remodelling such as the removal of osteophytes, but this is not necessary for device function.

There is no need to fix any device component in the trapezium.

The base plate glides over the trapezium and is preferentially attached via the ball and socket to the stem, decreasing the risk of dislocation out of the trapezium as is seen in other hemiarthroplasty designs.

The base plate is saddle shaped. It is convex-concave in keeping with the physiological shape of the trapezium bone.

The base plate comes in several different radii of curvature, facilitating different bone morphologies When a ball and socket is employed, the implant is a true articulating hemiarthroplasty. The device does not need to reconfigure to function.

During abduction-adduction, movement preferentially occurs at the ball and socket. This mimics the natural joint.

During flexion-extension, movement preferentially occurs that the base plate and bone interface, again mimicking the natural joint.

The ball and socket are within the metacarpal, mimicking the predominant point of rotation in the native joint.

The movement of the implant at two points may allow forces to be distributed more evenly across the joint.

Although the implant of the invention has been specifically described with the complex biomechanics of the CMC joint in mind, the concept of an articulating hemiarthroplasty may be clinically useful in other joints with complex biomechanics, such as multiple motions occurring simultaneously, a shifting axis of rotation, or a combination of both. Examples include the distal radioulnar joint (DRUJ), elbow, shoulder, and first metatarsal joints.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An implant for a mammalian bone joint for spacing a first bone of the joint from a second bone of the joint while allowing translational movement of the second bone in relation to the first bone, the implant comprising:
   (a) a first part configured for intramedullary engagement with an end of the second bone, the first part including a stem and a socket liner, wherein the socket liner is formed in a proximal end of the stem,
   (b) a second part having a platform configured for direct and non-engaging abutment with an end of the first bone and translational movement thereon, and
   (c) an articulating coupling provided between the first and second parts allowing controlled articulation of the first and second bones, the articulating coupling being connected to the first part at a location offset from a longitudinal axis of the first part.

2. The implant according to claim 1, wherein the articulating coupling is a ball and socket joint.

3. The implant according to claim 2, wherein a socket of the ball and socket joint is contained within the first part.

4. The implant according to claim 1, wherein the bone joint is one of a saddle joint, a metatarsophalangeal joint, or a glenohumeral joint.

5. The implant according to claim 1, wherein a proximal surface of the platform includes a concave curvature and a convex curvature.

6. The implant according to claim 5, wherein the concave curvature is along a longitudinal aspect of the platform.

7. The implant according to claim 5, wherein the convex curvature is along a transverse aspect of the platform.

8. The implant according to claim 1, wherein a length of the platform along a longitudinal aspect is longer than a width of the platform along a transverse aspect.

9. The implant according to claim 1, wherein a distal surface of the platform includes a convex curvature along a transverse aspect of the platform.

10. An implant for a mammalian first carpometacarpal joint for spacing a trapezium bone of the joint from a first metacarpal bone of the joint while allowing translational movement of the first metacarpal bone in relation to the trapezium bone, the implant comprising:
    (a) a distal part configured for intramedullary engagement with an end of the first metacarpal bone, the distal part including a stem and a socket liner, wherein the socket liner is formed in a proximal end of the stem,
    (b) a proximal part having a platform configured for non-engaging abutment of an end of the trapezium bone and translational movement thereon, the platform having a proximal surface including a convex curvature along a transverse aspect of the platform, and
    (c) an articulating coupling provided between the distal and proximal parts, allowing controlled articulation of the trapezium and first metacarpal bones.

11. The implant according to claim 10, wherein the proximal surface of the platform further includes a concave curvature along a longitudinal aspect of the platform.

12. The implant according to claim 10, wherein the articulating coupling is a ball and socket joint.

13. The implant according to claim 12, wherein a socket of the ball and socket joint is contained within the distal part.

14. The implant according to claim 10, wherein a length of the platform along a longitudinal aspect is longer than a width of the platform along a transverse aspect.

* * * * *